(12) United States Patent
Bird et al.

(10) Patent No.: US 9,044,307 B2
(45) Date of Patent: *Jun. 2, 2015

(54) ANKLE WALKER

(71) Applicant: Velocity Medical, LLC, St. Paul, MN (US)

(72) Inventors: John R. Bird, St. Paul, MN (US); Matthew J. Bird, St. Paul, MN (US); Dennis W. Baker, Rosemount, MN (US); Jeffrey J. Bollmann, Maplewood, MN (US)

(73) Assignee: Velocity Medical, LLC, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/053,993

(22) Filed: Oct. 15, 2013

(65) Prior Publication Data

US 2014/0046233 A1    Feb. 13, 2014

Related U.S. Application Data

(63) Continuation of application No. 13/231,636, filed on Sep. 13, 2011, now Pat. No. 8,574,181.

(51) Int. Cl.
*A61F 5/00* (2006.01)
*A61F 5/01* (2006.01)

(52) U.S. Cl.
CPC .................................. *A61F 5/0111* (2013.01)

(58) Field of Classification Search
USPC ...................... 602/13, 23–28; 128/882; 5/624
See application file for complete search history.

(56) References Cited

U.S. PATENT DOCUMENTS

| | | |
|---|---|---|
| 3,930,496 A | 1/1976 | Gibbons |
| 4,280,489 A | 7/1981 | Johnson, Jr. |
| 4,628,945 A | 12/1986 | Johnson, Jr. |
| D299,787 S | 2/1989 | Bates |

(Continued)

FOREIGN PATENT DOCUMENTS

| | | |
|---|---|---|
| DE | 101 63 706 A1 | 7/2003 |
| EP | 0 770 368 A1 | 5/1997 |

(Continued)

OTHER PUBLICATIONS

Air Trio™ Shell Ankle Walker, Designed for Stable Fractures of the Foot or Ankle, [online], [retrieved on Sep. 15, 2011], Retrieved from the Air Trio website using internet <http://pattersonmedical.com/content/PDF/spr/ElectronicLiterature/AirTrioSellSheet.pdf>.

(Continued)

*Primary Examiner* — Michael A. Brown
(74) *Attorney, Agent, or Firm* — IPLM Group, P.A.

(57) ABSTRACT

An ankle walker including an ankle shell, an inner lining, at least one bladder and at least one strap is provided. The ankle shell includes a base, a lower foot portion, a first and second side panel and a back panel. The lower foot portion extends upward from the base. The first side panel and second side panel extend from respective first and second portions of the lower foot portion. The back panel extends from a third portion of the lower foot portion and is positioned between the first and second side panels. The ankle shell has a first slot separating the first side panel from the back panel and a second slot separating the second side panel from the back panel. At least one of the first and second slots has a height that is at least one half the height of the ankle walker.

13 Claims, 26 Drawing Sheets

(56) References Cited

U.S. PATENT DOCUMENTS

| | | | |
|---|---|---|---|
| 4,966,134 A | 10/1990 | Brewer | |
| 5,044,360 A | 9/1991 | Janke | |
| 5,125,400 A | 6/1992 | Johnson, Jr. | |
| 5,213,564 A | 5/1993 | Johnson, Jr. et al. | |
| 5,250,021 A | 10/1993 | Chang | |
| 5,328,445 A | 7/1994 | Spahn et al. | |
| 5,348,530 A | 9/1994 | Grim et al. | |
| 5,425,701 A * | 6/1995 | Oster et al. | 602/23 |
| 5,489,259 A | 2/1996 | Jacobs et al. | |
| 5,503,622 A | 4/1996 | Wehr | |
| 5,564,143 A | 10/1996 | Pekar et al. | |
| 5,577,998 A | 11/1996 | Johnson, Jr. et al. | |
| 5,620,411 A | 4/1997 | Schumann et al. | |
| 5,717,996 A | 2/1998 | Feldmann | |
| 5,833,639 A | 11/1998 | Nunes et al. | |
| 5,857,987 A | 1/1999 | Habermeyer | |
| 6,021,780 A | 2/2000 | Darby | |
| 6,083,184 A | 7/2000 | Kenosh | |
| 6,245,035 B1 | 6/2001 | Schrijver | |
| 6,375,633 B1 | 4/2002 | Endress et al. | |
| 6,397,400 B1 | 6/2002 | Hassler et al. | |
| D473,654 S | 4/2003 | Iglesias et al. | |
| 6,572,571 B2 | 6/2003 | Lowe | |
| 6,582,382 B2 | 6/2003 | Domanski et al. | |
| 6,613,006 B1 | 9/2003 | Asherman | |
| 6,682,497 B2 * | 1/2004 | Jensen et al. | 602/27 |
| 6,689,079 B2 | 2/2004 | Flick et al. | |
| D500,855 S | 1/2005 | Pick et al. | |
| D534,712 S | 1/2007 | Darby, II | |
| 7,285,104 B2 | 10/2007 | Hassler et al. | |
| 7,303,538 B2 | 12/2007 | Grim et al. | |
| RE40,363 E | 6/2008 | Grim et al. | |
| 7,455,651 B2 | 11/2008 | Mollica | |
| 7,458,948 B2 | 12/2008 | Drennan | |
| 7,618,388 B1 | 11/2009 | Chan | |
| 7,713,224 B1 | 5/2010 | Peters et al. | |
| 7,896,828 B1 | 3/2011 | Shirley | |
| D640,791 S | 6/2011 | Anderson et al. | |
| 8,002,724 B2 * | 8/2011 | Hu et al. | 602/27 |
| 8,007,456 B2 | 8/2011 | Stano | |
| 8,021,317 B2 | 9/2011 | Arnold et al. | |
| 8,142,381 B1 | 3/2012 | Birnbaum | |
| D662,598 S | 6/2012 | Anderson et al. | |
| 8,435,198 B2 | 5/2013 | Weissenböck et al. | |
| 8,454,546 B2 | 6/2013 | Campos et al. | |
| 2002/0128574 A1 | 9/2002 | Darby | |
| 2005/0171461 A1 * | 8/2005 | Pick | 602/27 |
| 2006/0229541 A1 | 10/2006 | Hassler et al. | |
| 2007/0191749 A1 | 8/2007 | Barberio | |
| 2009/0069735 A1 | 3/2009 | Chiang | |
| 2009/0216167 A1 | 8/2009 | Harris | |
| 2009/0227927 A1 | 9/2009 | Frazer | |
| 2009/0306565 A1 | 12/2009 | Chan | |
| 2011/0009791 A1 | 1/2011 | Hopmann | |

FOREIGN PATENT DOCUMENTS

| | | |
|---|---|---|
| WO | WO 2005/074834 A2 | 8/2005 |
| WO | WO 2007/008545 A2 | 1/2007 |
| WO | WO 2010/094052 A1 | 8/2010 |

OTHER PUBLICATIONS

Aircast, XP Walker™ (extra pneumatic), [online], [retrieved on Sep. 15, 2011], Retrieved using internet <http://www.aircast.com/index.asp/fuseaction/products.detail/cat/2/id/76.>.

Equalizer® Air Walker, AliMed, Medical and Ergonomic Products for Healthcare, Business, and Home, [online], [retrieved on Sep. 15, 2011], Retrieved using the AliMed internet site, < http://www.alimed.com/equalizer-air-walker.html>.

International Search Report for PCT Application PCT/US2012/054634, mailed Feb. 20, 2013, 4 pages.

StepLite® Easy Strider Ankle Walkers, FLA Orthopedics, Inc., [online], [retrieved on Sep. 15, 2011], Retrieved from the FLA Orthopedics website using <http://flaorthopedic.com/pr_easystrider.asp>.

VACO® cast—VACOcast Pro Achilles, [online], [retrieved on Mar. 27, 2012], [retrieved from <http://www.vacocast.com/pro/>], 6 pages.

VACO® cast—VACOcast Pro Diabetic, [online], [retrieved on Mar. 27, 2012], [retrieved from <http://www.vacocast.com/diabetic/>], 5 pages.

VACO® cast—VACOcast Fit, [online], [retrieved on Mar. 26, 2012], [retrieved from <http://www.vacocast.con/fit/>], 3 pages.

Supplementary European Search Report, European Patent Application No. 12831839.1, mailed Mar. 12, 2015.

\* cited by examiner

ANKLE WALKER

CROSS REFERENCE TO RELATED APPLICATION

This application claims priority to and is a Continuation Application of U.S. patent application Ser. No. 13/231,636 filed Sep. 13, 2011, now Pat. No. 8,574,181 issued Nov. 5, 2013, the disclosure of which is incorporated in its entirety by reference herein.

BACKGROUND

Injuries to the lower leg, such as a fracture or break in an ankle, typically require the injured area to be immobilized for proper healing to take place. One method of immobilizing an area is with a cast made of plaster of Paris or modern variants. A typical cast can impede the mobility of the patient. With some types of injuries, an orthotic walking cast can be used. An orthotic walking cast allows the patient better mobility while still allowing the injury to heal. Some walking casts are made to be removable. However, it can be difficult to get a removable walking cast on and off. It can also be difficult to get the walking cast to fit properly so that enough support is provided to properly immobilize the lower leg of the patient.

For the reasons stated above and for other reasons stated below which will become apparent to those skilled in the art upon reading and understanding the present specification, there is a need in the art for an effective and efficient orthopedic ankle walker that is easy to get on and off and can be efficiently fit to a patient's lower leg.

SUMMARY OF INVENTION

The above-mentioned problems of current systems are addressed by embodiments of the present invention and will be understood by reading and studying the following specification. The following summaries are made by way of example and not by way of limitation. They are merely provided to aid the reader in understanding some of the aspects of the invention.

In one embodiment, a walker shell is provided. The walker shell includes a base, first and second side panels and a back panel. The base is configured and arranged to support the weight of a patient using the walker shell. The first side panel is connected to the base and terminates in a first side panel top edge. The second side panel is connected to the base and terminates in a second side panel top edge. The second side panel is positioned across the base from the first side panel. The back panel is connected to the base and terminates in a back panel top edge. The back panel is positioned between the first and second side panels. The first side panel and the back panel have a first slot there between and the second side panel and the back panel having a second slot there between. The walker shell has a height extending between the base and the first and second side panel top edges. The first and second slots extend at least one half the height of the walker shell to allow the back panel to move relative to the first and second side panels thereby allowing for the walker shell to be easily positioned about a patient's calf when the patient is putting on the walker shell.

In another embodiment, an ankle walker is provided, the ankle walker includes an ankle shell, an inner lining, at least one bladder and at least one strap. The ankle shell includes a base, a lower foot portion, a first and second side panel and a back panel. The base is configured and arranged to support the weight of a patient using the walker shell. The lower foot portion extends upward from the base proximate a portion of an outer perimeter of the base. The first side panel extends from a first portion of the lower foot portion. The second side panel extends from a second portion of the lower foot portion. The second side panel is positioned across the base from the first side panel. The back panel extends from a third portion of the lower foot portion. The back portion is positioned between the first and second side panels. The ankle shell has a first slot separating the first side panel from the back panel and a second slot separating the second side panel from the back panel. The ankle walker further has a height that extends between the base and an upper edge of at least one of the first and second side panels of the walker shell. At least one of the first and second slots has a height that is at least one half of the height of the ankle walker. Further, wherein the base, lower foot portion, first and second side panels and the back panel form an ankle shell cavity in which a patient's lower foot is received. The inner lining is configured and arranged to fit within the ankle shell cavity. The at least one bladder is configured and arranged to be selectively inflated. The at least one bladder is positioned within the ankle shell cavity. Moreover, the at least one strap is configured and arranged to secure the ankle shell around a patient's lower leg.

In still another embodiment, another ankle walker is provided. This ankle walker includes an ankle shell, an inner lining, at least one bladder and at least one strap. The ankle shell includes a base, a lower foot portion, first and second side panels and a back panel. The base is configured and arranged to support the weight of a patient using the walker shell. The lower foot portion extends upward from the base proximate a portion of an outer perimeter of the base. The first side panel extends from a first portion of the lower foot portion. The first side panel has a first malleolus concavity positioned to receive a malleolus of a foot of a patient positioned in the ankle walker. The first malleolus concavity is located proximate the lower foot portion. The second side panel extends from a second portion of the lower foot portion. The second side panel is positioned across the base from the first side panel. The second side panel has a second malleolus concavity positioned to receive a malleolus of an ankle of a patient positioned in the ankle walker. The second malleolus concavity is located proximate the lower foot portion. The back panel extends from a third portion of the lower foot portion. The back portion is positioned between the first and second side panels. The ankle shell has a first slot separating the first side panel from the back panel and a second slot separating the second side panel from the back panel such that the back panel can move independent of the first and second side panels. The first slot extends from an upper edge of the first side panel to at least the first malleolus concavity. The second slot extends from an upper edge of the second side panel to at least the second malleolus concavity. The base, lower foot portion, first and second side panels and back panel form an ankle shell cavity in which a patient's lower foot is received. The inner lining is configured and arranged to fit within the ankle shell cavity. The at least one bladder is configured and arranged to be selectively inflated, the at least one bladder is positioned within the ankle shell cavity. The at least one strap is configured and arranged to secure the ankle shell around a patient's lower leg.

BRIEF DESCRIPTION OF THE DRAWINGS

The present invention can be more easily understood and further advantages and uses thereof will be more readily apparent, when considered in view of the detailed description and the following figures in which.

In accordance with common practice, the various described features are not drawn to scale but are drawn to emphasize specific features relevant to the present invention. Reference characters denote like elements throughout Figures and text.

DETAILED DESCRIPTION

In the following detailed description, reference is made to the accompanying drawings, which form a part hereof, and in which is shown by way of illustration specific embodiments in which the inventions may be practiced. These embodiments are described in sufficient detail to enable those skilled in the art to practice the invention, and it is to be understood that other embodiments may be utilized and that changes may be made without departing from the spirit and scope of the present invention. The following detailed description is, therefore, not to be taken in a limiting sense, and the scope of the present invention is defined only by the claims and equivalents thereof.

Figure 1:
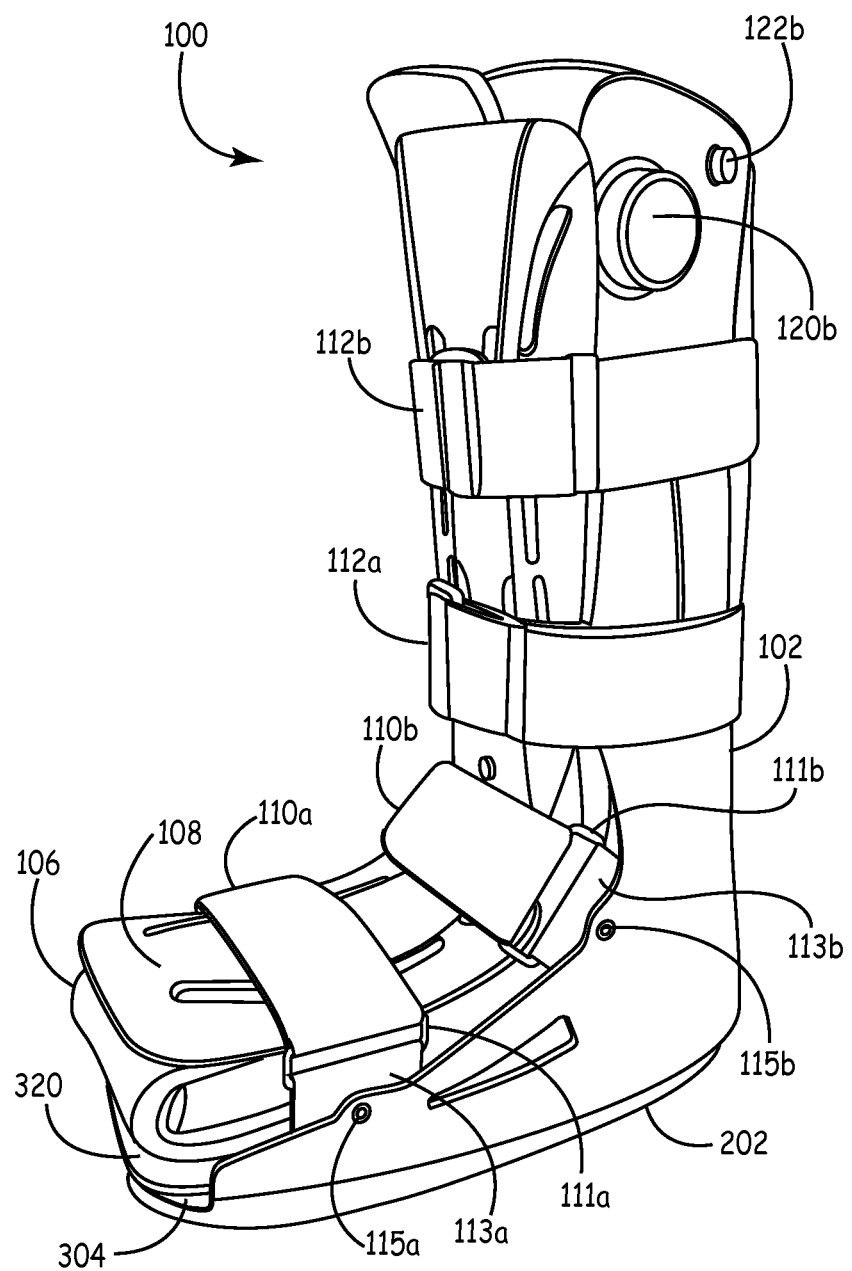
FIG. 1 is a side perspective view of an ankle walker of one embodiment of the present invention.

Embodiments of the present invention provide an ankle walker (walking cast) that is used to support a lower leg of a patient. In embodiments, the ankle walker is designed to be put on easily without aggravating the injury the patient is trying to recover from and to provide adequate support to the patient to allow the injury to heal. Referring to FIG. 1, a side perspective view of an ankle walker 100 of one embodiment is illustrated. The ankle walker 100 includes a walker shell 102, an inner lining 106, a front panel 108 and straps 110a, 110b, 112a and 112b. Also illustrated in FIG. 1 is an air inflation pump 120b that is designed to selectively inflate a bladder (described below) that is positioned around the patient's ankle to selectively provide stability and an air release valve 122b to selectively release air out of the bladder to deflate the bladder. The straps 110a, 110b, 112a and 112b, securely hold the walker shell 102 and front panel 108 around a patient's lower leg. The lower straps 110a and 110b are selectively coupled across a lower foot portion 209 (illustrated in FIG. 2) of the walker shell 102. In the embodiment of FIG. 1, the lower straps 110a and 110b are coupled to the lower foot portion 209 of the walker shell via respective buckle systems that include buckle members 111a and 111b, connection members 113a and 113b and rivets 115a and 115b. In one embodiment, the connection members 113a and 113b are made of a fabric. Similar buckle systems are connected to a side of the lower portion of the walker shell 102 not shown in FIG. 1. Each of the straps 110a, 110b, 112a and 112b in an embodiment use a hook and loop connection system to connect a portion of each strap to another portion of the strap.

Figure 2:
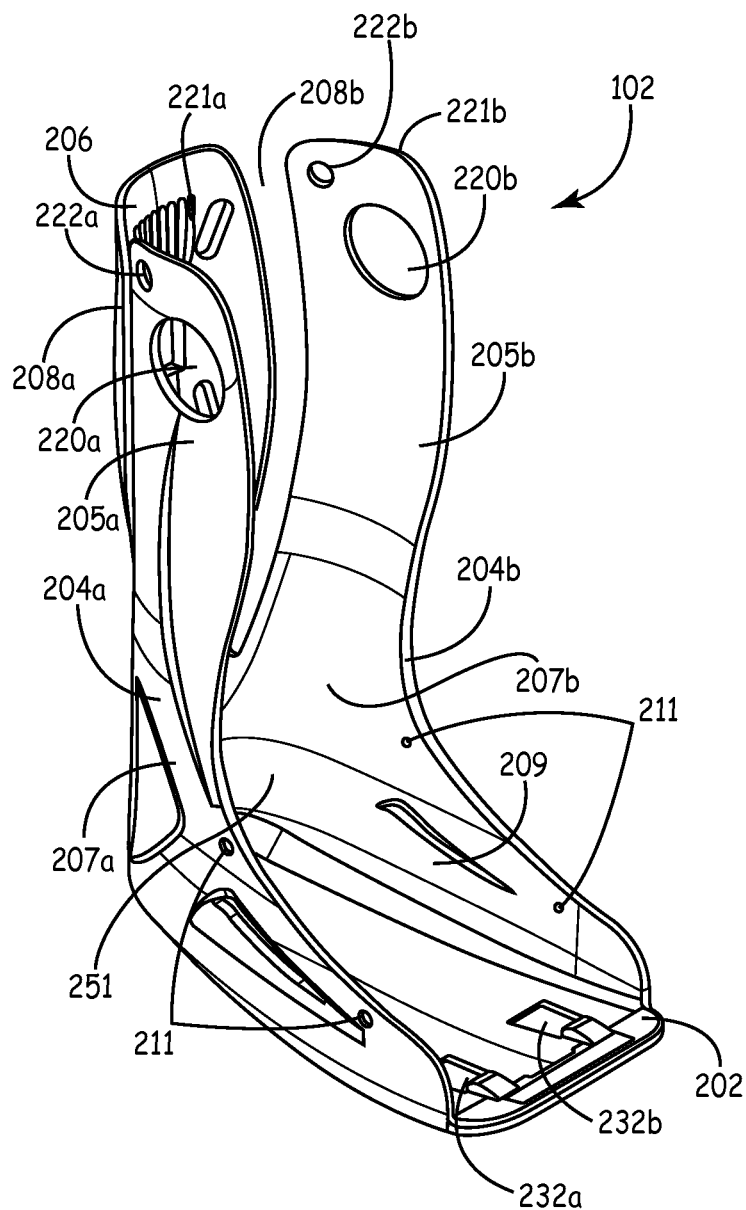
FIG. 2 is a side perspective view of a walker shell of one embodiment of the present invention.

FIG. 2 illustrates a side perspective view of the walker shell 102 of an embodiment. The walker shell 102 includes first and second side panels 204a and 204b, a back panel 206, the lower foot portion 209 and a base 202. The side panels 204a and 204b have upper portions 205a and 205b that extend from upper edges 221a and 221b to lower portions 207a and 207b. The lower portions 207a and 207b extend into the lower foot portion 209 of the walker shell 102. The first and second side panels 204a and 204b and back panel 206 are designed to be positioned around a lower leg portion of the patient and the lower foot portion 209 is designed to fit around a foot of the patient. In particular, the base 202, the lower foot portion 209, the first and second side panels 204a and 204b and back panel 206 form an ankle shell cavity 251 in which a patient's lower foot is received. As FIG. 2 further illustrates, in one embodiment, the side panels 204a and 204b include air pump passages (apertures) 220a and 220b and relief valve passages (apertures) 222a and 222b located proximate top edges 221a and 221b of the respective side panels 204a and 204b. Although, the air pump apertures 220a and 220b and relief valve apertures 222a and 222b are located proximate the top edges 221a and 221b of the respective side panels 204a and 204b in the embodiment shown, they can be located in any location on the respective side panels 204a and 204b. The air pump apertures 220a and 220b provide a passage for an air inflation pump 120 to a respective bladder 402a and 402b (described below) positioned within the ankle shell cavity 251. The relief valve apertures 222a and 222b provide passages for a relief valve 122b to the respective bladder. Further illustrated in FIG. 2 is connection passages 211 selectively spaced in an upper portion of the lower foot portion 209 of the walker shell 102. The connection passages 211 are used to connect straps as further discussed below. FIG. 2 also illustrates foot support connection passages 232a and 232b that are designed to keep in place a foot support and are discussed further below.

Figure 3A:
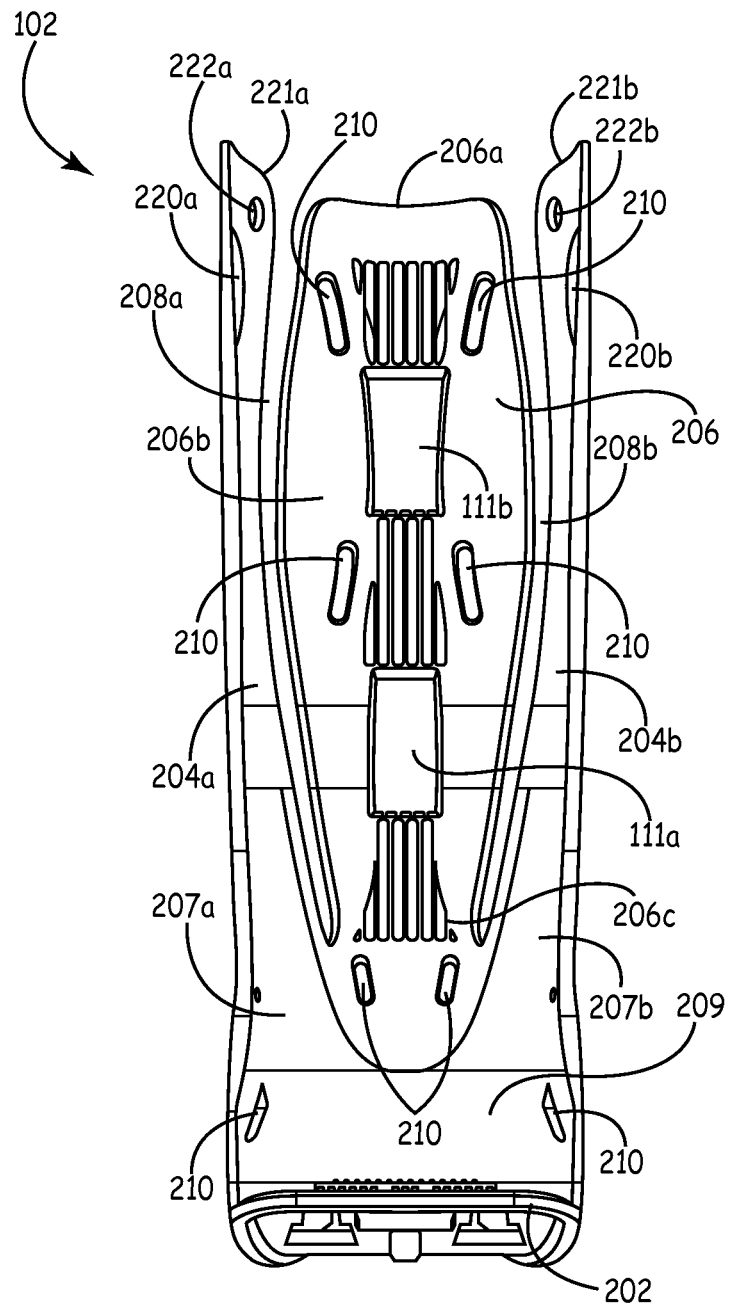
FIG. 3A is a front view of the walker shell of FIG. 2.
Figure 3B:
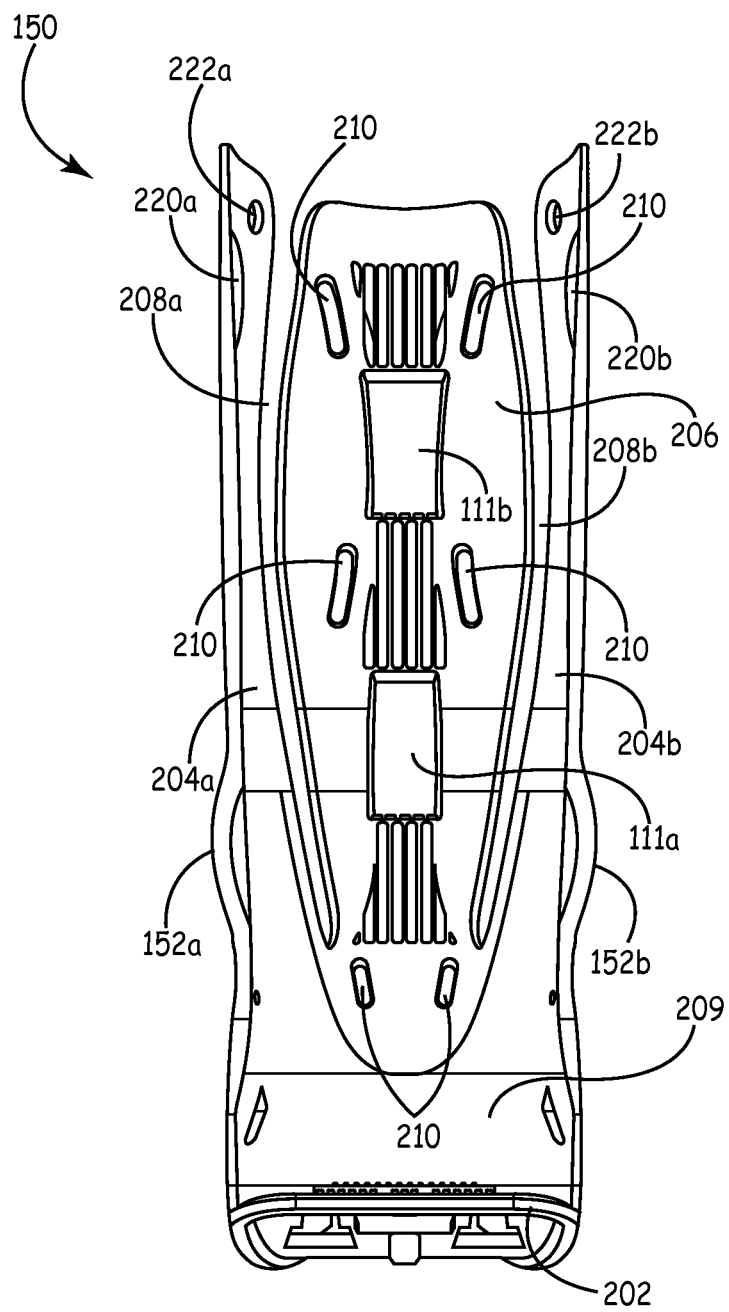
FIG. 3B is a front view of another embodiment of a walker shell of an embodiment of the present invention.

As the front view of the walker shell 102 illustrates in FIG. 3A, a first slot 208a and a second slot 208b separates the first side panel 204a and the second side panel 204b from the back panel 206. In particular, slot 208a separates the first side panel 204a from the back panel 206 and slot 208b separates the second side panel 204b from the back panel 206. The back panel includes a top edge 206a, a mid portion 206b and a lower portion 206c. The lower portion 206c of the back panel 206 extends into the lower portion 209 of the walker shell 102. In the embodiment of FIG. 3A, the mid portion 206b of the back panel 206 has a width that is greater than a width of the back panel 206 proximate the top edge 206a and the lower portion 206c. The slots 208a and 208b of FIG. 3A extend from the top edges 221a and 221b of the side panels 204a and 204b and the top edge 206a of the back panel 206 to lower portion 209 of the walker shell 102. In one embodiment, the slots 208a and 208b extend down past a position where a patient's malleolus would be located when wearing the ankle walker 100. For example, referring to FIG. 3B, a different embodiment of the walker shell 150 is illustrated. In this embodiment of the walker shell 150, malleolus concavities 152a and 152b are formed in the side panels 204a and 204b proximate the lower foot portion 209 of the walker shell 150. The malleolus concavities 152a and 152b are concavities in the interior surface of the respective side panels 204a and 204b in which a patient's malleolus' fit within. From the outside of the walker shell 150 they look like bulges and can be referred to as malleolus concavities. The malleolus concavities 152a and 152b provide added room for the patient's malleolus. The malleolus is the bony protuberance on either side of the ankle at the lower ends of the respective fibula and tibia bones. The malleolus concavities 152a and 152b in the walker shell 150 provide added comfort for the patient. As illustrated in FIG. 3B, the first slot 208a and the second slot 208b in this embodiment extend down past the malleolus concavities 152a and 152b.

The slots 208a and 208b in the embodiments of FIGS. 3A and 3B extending down to the lower portion 209 of the walker shells 102 and 150 allow the back panel 206 to be flexible when the patient is placing their foot in the ankle walker 100. In particular, the flexible back panel 206 eases the ankle walker over the calf of the patient when the patient's lower leg is being placed in the ankle walker 100. In an embodiment, the slots 208a and 208b extend at least half the height of the walker shell 102 or 150 and in one embodiment the slots extend approximately two thirds of the height of the walker shell 102 or 150. In some embodiments the walker shells 102 and 150 are made of a plastic (polymer material) in a thermo forming process so that the back panel flexes in relation to the lower portion 209 of the walker shell 102 without breaking.

Figure 4:
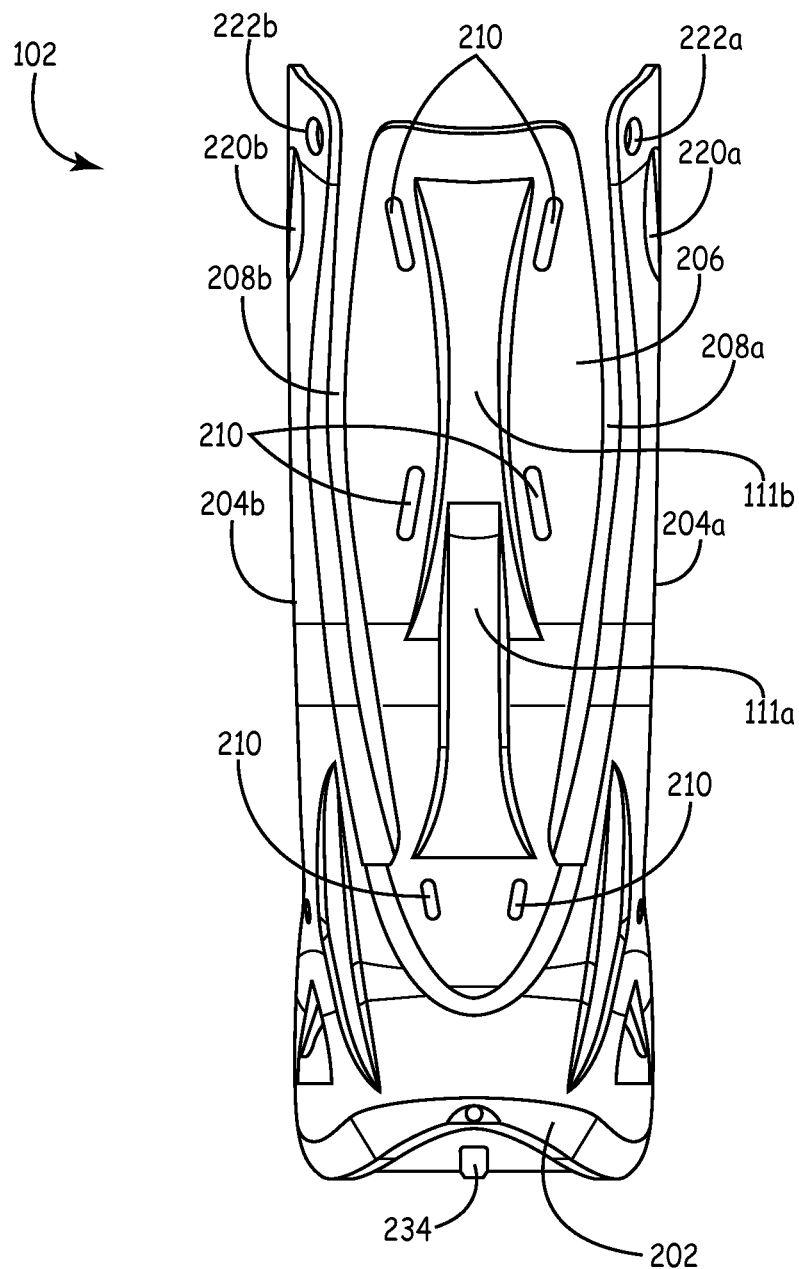
FIG. 4 is a back view of the walker shell of FIG. 2.

Referring back to FIG. 3A, the walker shell 102 further includes vents 210 that provide passages through the back panel 206 and the lower portion 209 of the walker shell 102. The vents 210 allow venting of the patient's foot in the walker shell 102. Also illustrated in FIG. 3A are strap guides 111a and 111b that are formed in the back panel 206. The strap guides 111a and 111b are designed to receive the respective straps 112a and 112b. The strap guides 111a and 111b hold the respective straps 112a and 112b in position in relation to the back panel 206. FIG. 4 illustrates a back view of the embodiment of the walker shell illustrated in FIG. 2. This view further illustrates the shape of the back panel 206 created by slots 208a and 208b. As discussed above in regards to FIG. 3A, the back panel 206 includes a top edge 206a, a mid portion 206b and a bottom portion 206c. The mid portion 206b is wider than the top edge 206a and the bottom portion 206c. As also discussed above the length of the slots 208a and 208b allow the back portion to pivot out from the lower portion 209 of the walker shell 102 to allow for easy installation of the ankle walker 100 on the patient's lower foot. Also illustrated in FIG. 4 is a holding rail guide 234 that is further discussed below.

Figure 5:
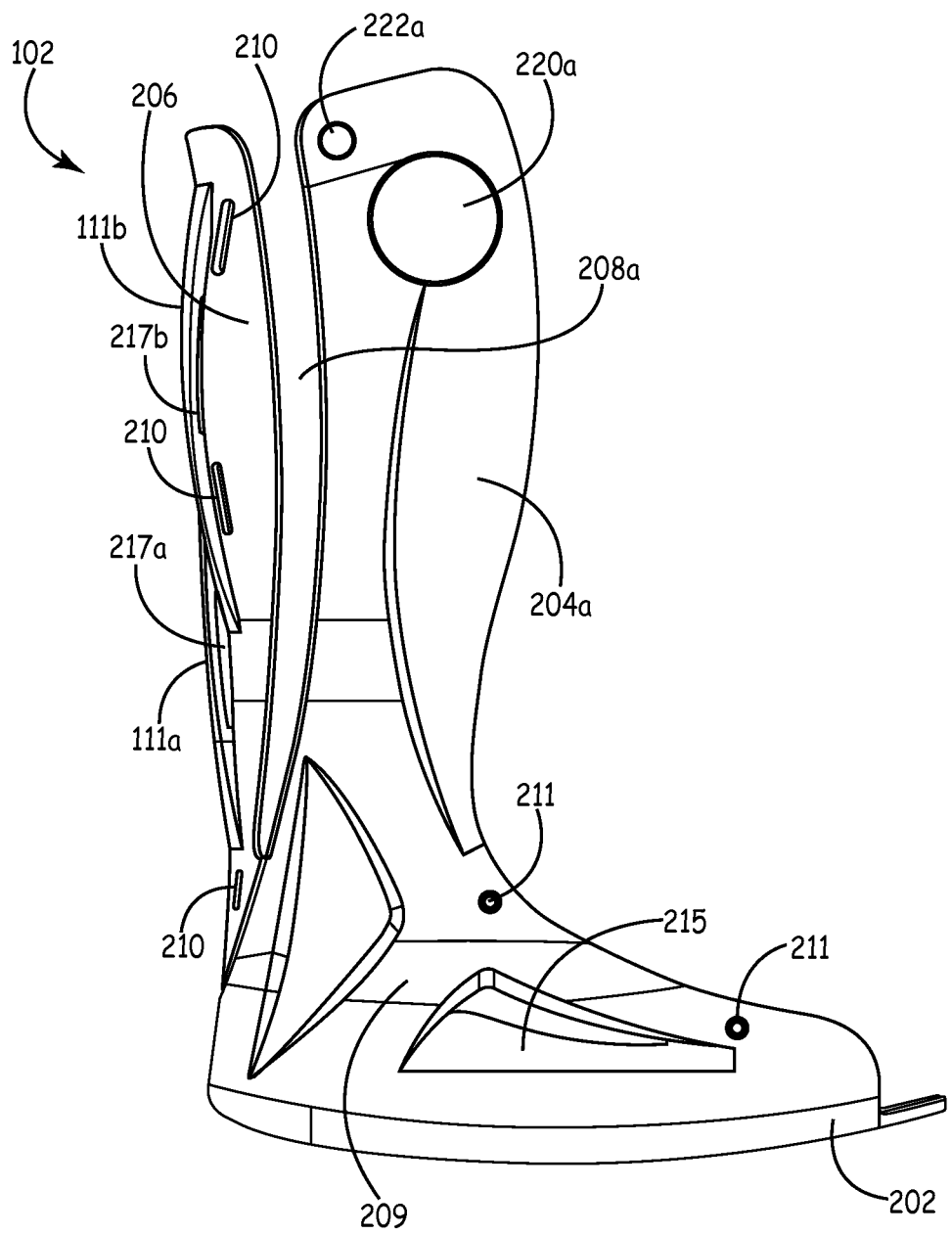
FIG. 5 is a side view of the walker shell of FIG. 2.
Figure 6:
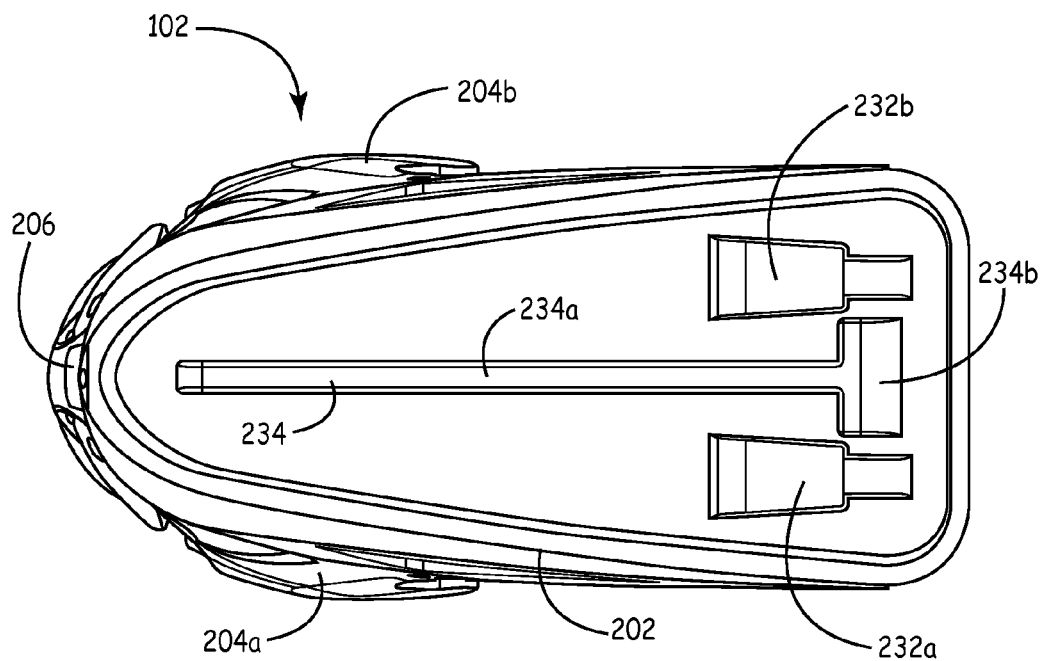
FIG. 6 is a bottom view of the walker shell of FIG. 2.

FIG. 5 illustrates a side view of the walker shell 102 of FIG. 2. In the side view of FIG. 5, the first side panel 204a and lower portion 209 of the walker shell 102 is shown as well as the first slot 208a, the back panel 206 and the base 202. This view illustrates that the lower portion 209 of the walker shell 102 includes a lower vent 215. Also illustrated in this view are strap passages 217a and 217b of the respective first and second strap guides 111a and 111b. Straps 112a and 112b are passed through the respective strap passages 217a and 217b to retain the straps 112a and 112b in a desired position. FIG. 6 illustrates a bottom view of the walker shell 102. The bottom view illustrates the foot support connection passages 232a and 232b and the holding guide rail 234. The holding guide rail 234 is generally in a T-shape.

Figure 7A:
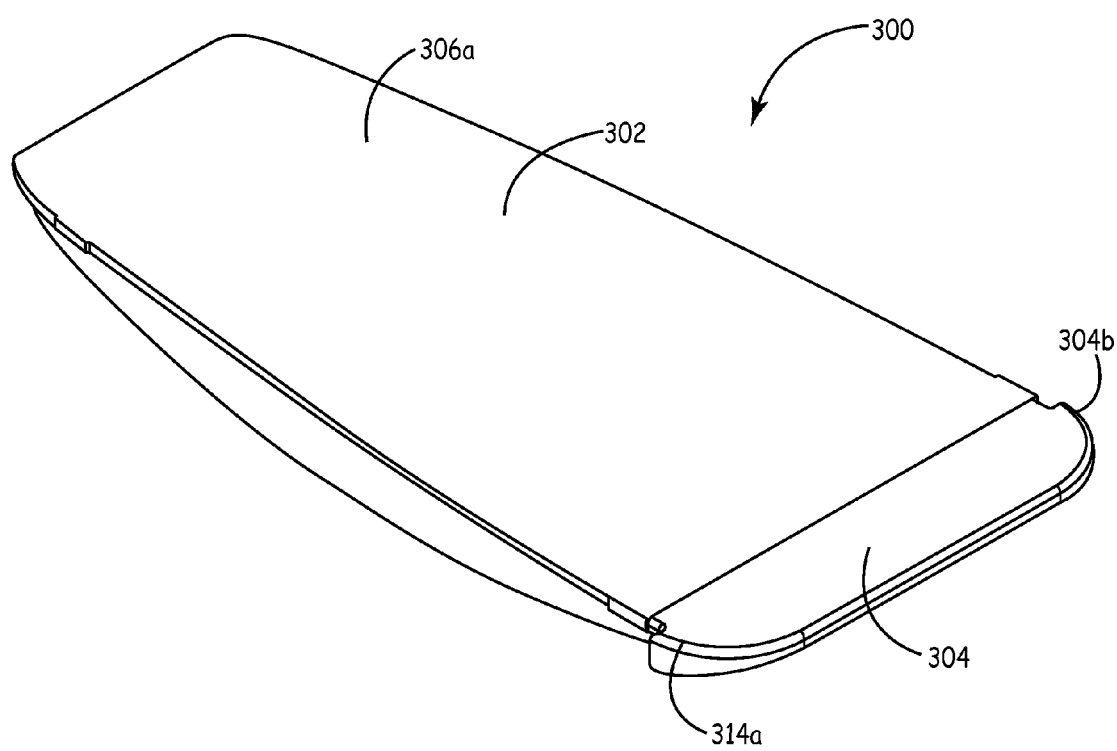
FIG. 7A is a top perspective view of a foot support member of one embodiment of the present invention.
Figure 7B:
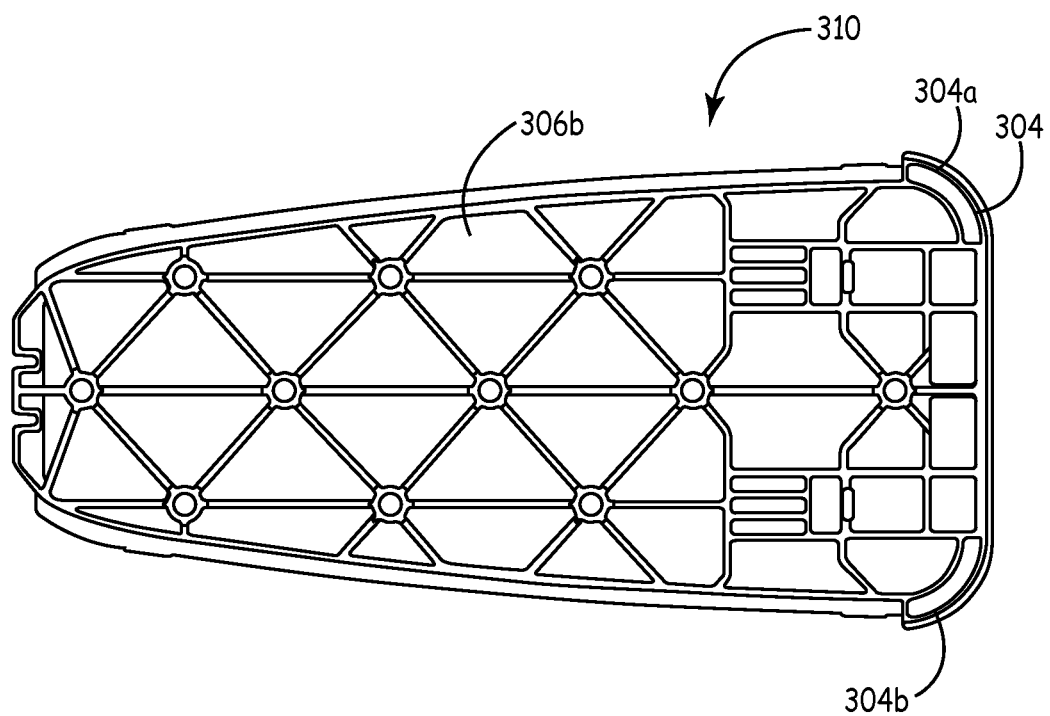
FIG. 7B is a bottom view of the foot support member of FIG. 7A.
Figure 7C:
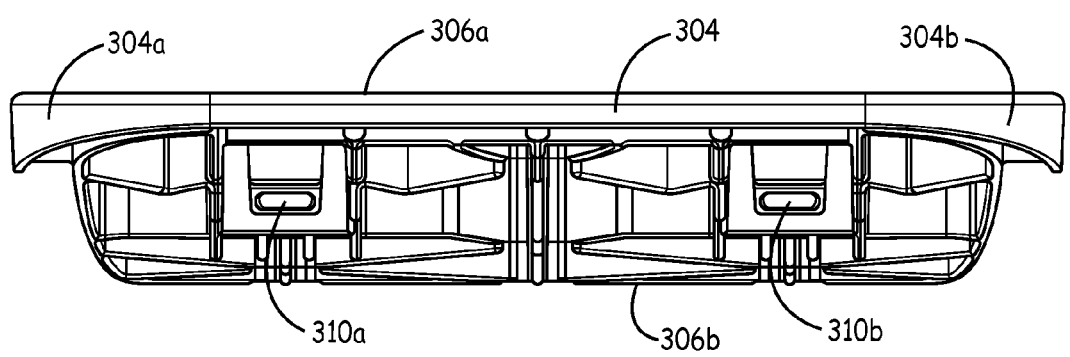
FIG. 7C is a front view of the foot support member of FIG. 7A.

FIGS. 7A through 7C illustrate a foot support member 300 of an embodiment that is designed to fit in the ankle shell cavity 251 of the walker shell 102 over the base 202. In particular, FIG. 7A illustrates a top perspective view of the foot support 300 of one embodiment, FIG. 7B illustrates a bottom view of the foot support member 300 and FIG. 7C illustrates a front view of the foot support member 300. The foot support member 300 includes a main support portion 302 and a front portion 304. The foot support member 300 fits in the walker shell 102 and is positioned on top of the base 202. In an embodiment, the front portion 304 is configured to be positioned proximate the front of the walker shell 102 such that front side portions 304a and 304b are positioned in front of portions the lower portion 209 of the walker shell 102. Base connection members 310a and 310b on a bottom side 306b of the foot support member engage respective foot support connection passages 232a and 232b (illustrated in FIG. 2) of the walker shell 102 to connect the foot support member 300 to the base 202. In one embodiment, a layer of foam 320 (illustrated in FIGS. 1 and 11) is coupled to a top side 306a of the foot support 300 to provide added comfort for the patient.

Figure 8A:
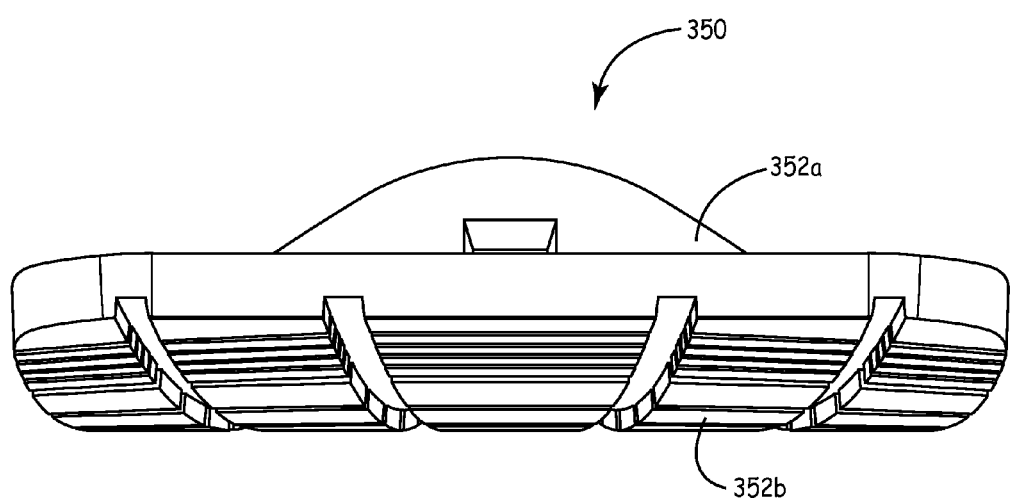
FIG. 8A is a front perspective view of a sole of one embodiment of the present invention.
Figure 8B:
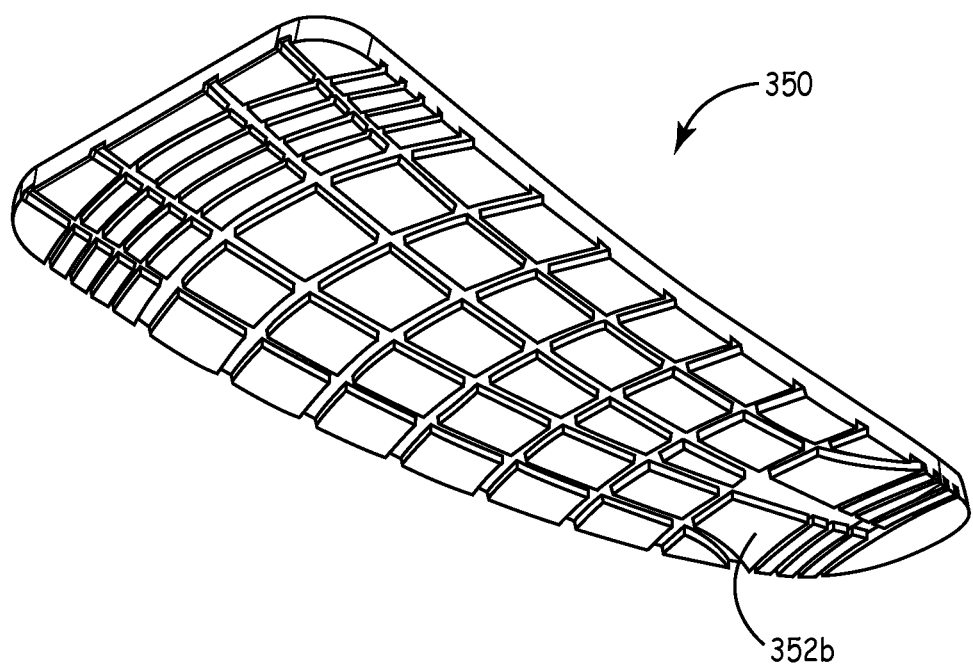
FIG. 8B is a bottom perspective view of the sole of FIG. 8A.
Figure 8C:
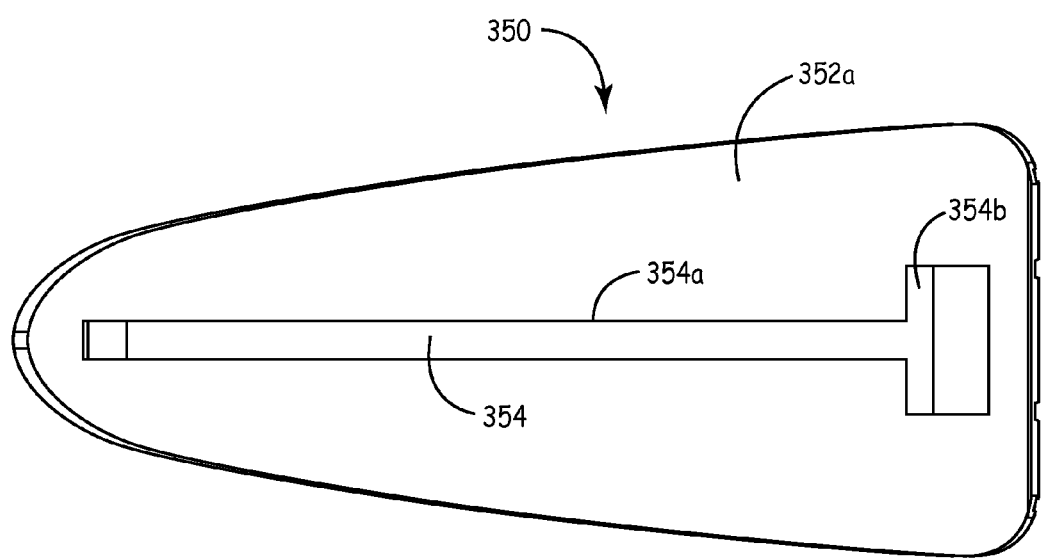
FIG. 8C is a top view of the sole of FIG. 8A.

Embodiments include a sole, such as sole 350 illustrated in FIG. 8A. The sole is made of a pliable material such as, but not limited to, a rubber material. The sole includes an upper side 352a and a lower side 352b. Referring to FIG. 8B, the lower side 352b of the sole 350 includes a tread pattern. The upper side 352a of the sole 350 is illustrated in FIG. 8C. The upper side 352a includes a holding rail 354 that includes a first portion 354a that extends generally a length of the sole 350 and a second portion 354b proximate the front of the sole 350. The first portion 354a and the second portion 354b of the holding rail 354 form generally a T-shape. The holding rail 354 on the upper side 352a of the sole 350 is received in the holding rail guide 234 of the bottom of the base 202 of the walker shell 102 (illustrated in FIG. 6). In particular, the first portion 354a of the holding rail 354 is received in the first portion 234a of the holding rail guide 234 and the second portion 354b of the holding rail 354 is received in the second portion 234b of the holding rail guide 234. This arrangement retains the sole 350 in a select position in relation to the base 202 of the walker shell 102. In an embodiment, the sole 350 is further attached to the base 202 of the walker shell 102 with an adhesive.

Figure 9A:
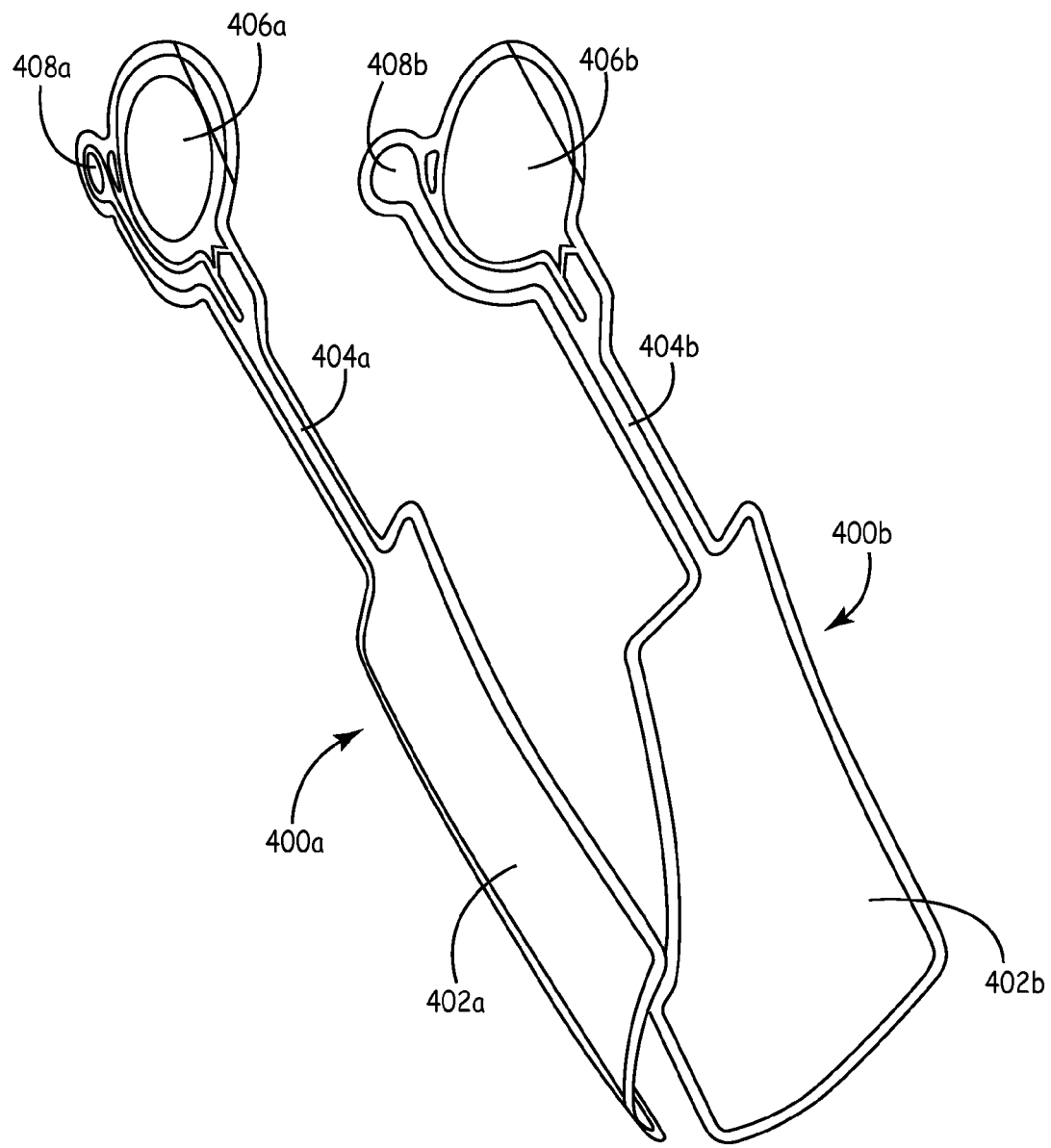
FIG. 9A is a side perspective view of bladder inflation assemblies of one embodiment of the present invention.
Figure 9B:
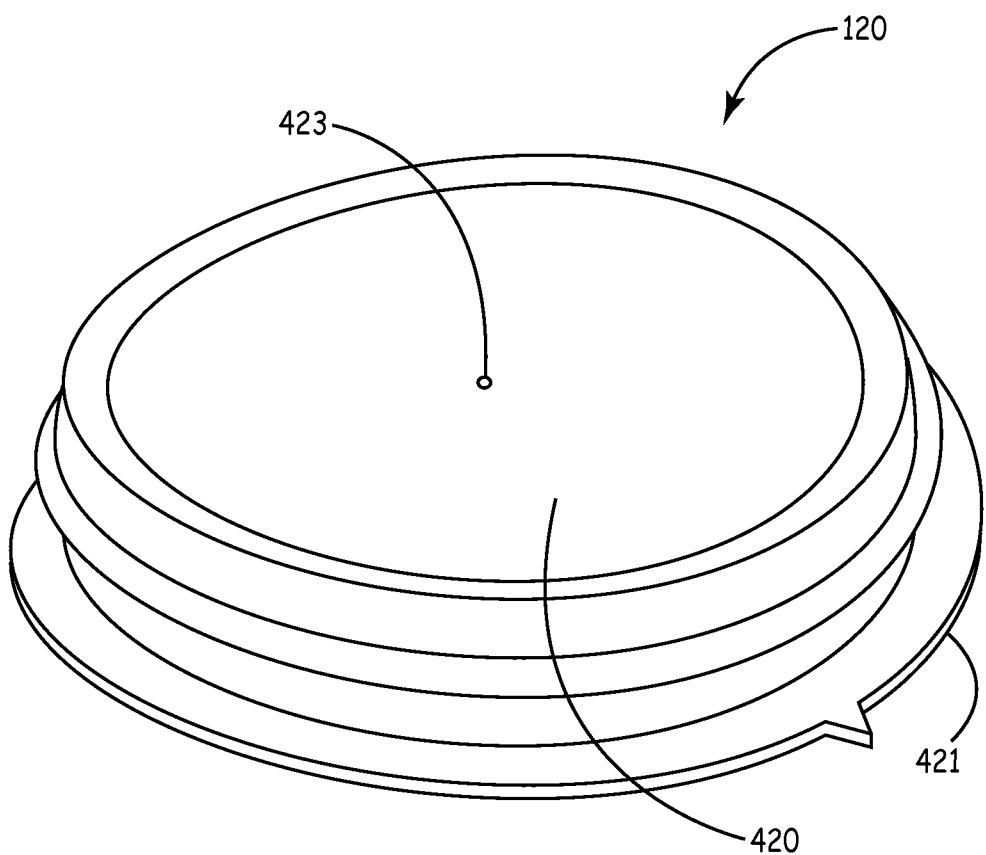
FIG. 9B is a side perspective view of an inflation pump of one embodiment of the present invention.
Figure 9C:
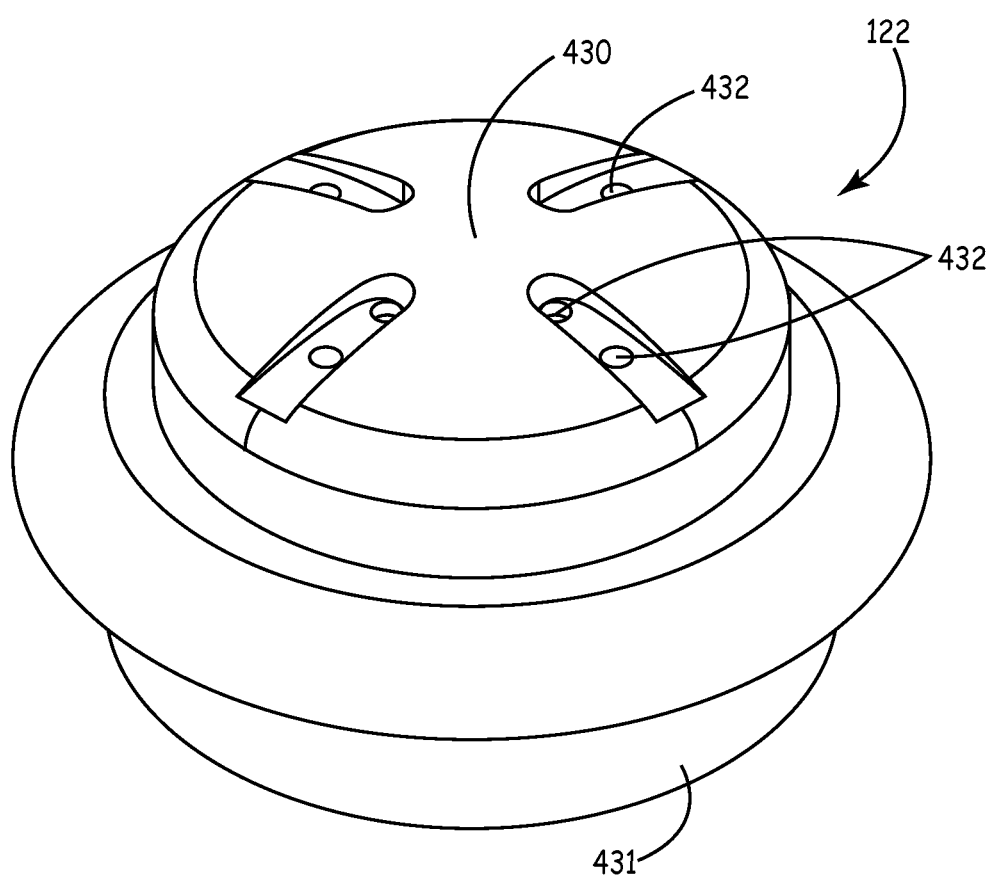
FIG. 9C is a side perspective view of an air release valve of one embodiment of the present invention.

Referring to FIG. 9A, bladder inflation assemblies 400a and 400b of an embodiment are illustrated. Each bladder assembly 400a and 400b includes a bladder 402a and 402b. In one embodiment the bladders 402a and 402b are made of a plastic polymer material that is designed to retain pumped air. Air paths 404a and 404b are in fluid communication with the respective bladders 402a and 402b. The air paths 404a and 404b are in turn in fluid communication with respective pump connection portions 406a and 406b and respective release valve connection portions 408a and 408b. An example of an air inflation pump (generally designated as 120) is illustrated in FIG. 9B. The inflation pump 120 includes a pumping portion 420 designed to be repeatedly depressed to pump air into a respective bladder 402. The pumping portion 420 includes a small central aperture 423 that allows the pumping portion 420 to retain its non-depressed shape after a depression has occurred. The inflation pump 120 further includes a pump base 421 that is designed to be coupled to a respective pump connection portion 406 of a bladder assembly 400. FIG. 9C illustrates an example of an air release valve (generally designated as 122). The air release valve 122 includes a depressing portion 430 and a base 431. The base 431 is coupled to a respective release valve connection portion 408a or 408b. Inside the air release valve 122 is an internal valve (not shown) that is designed to only allow air in through air ports 432. Once the depressing portion 430 of the air release valve 122 is depressed, air is allowed to pass around the internal valve and escape out the air ports 432. Hence in use, when the pumping portion 420 of the air inflation pump 120 is activated, air is pulled into the respective air bladder assembly 400a or 400b through the air ports 432 and one way internal valve thereby inflating the respective bladder 402a or 402b around a patient's ankle. When it is desired to remove some of the air in the bladder 402a or 402b, the depressing portion 430 of the air release valve 122 is depressed allowing air to escape out of the air ports 432.

Figure 10:
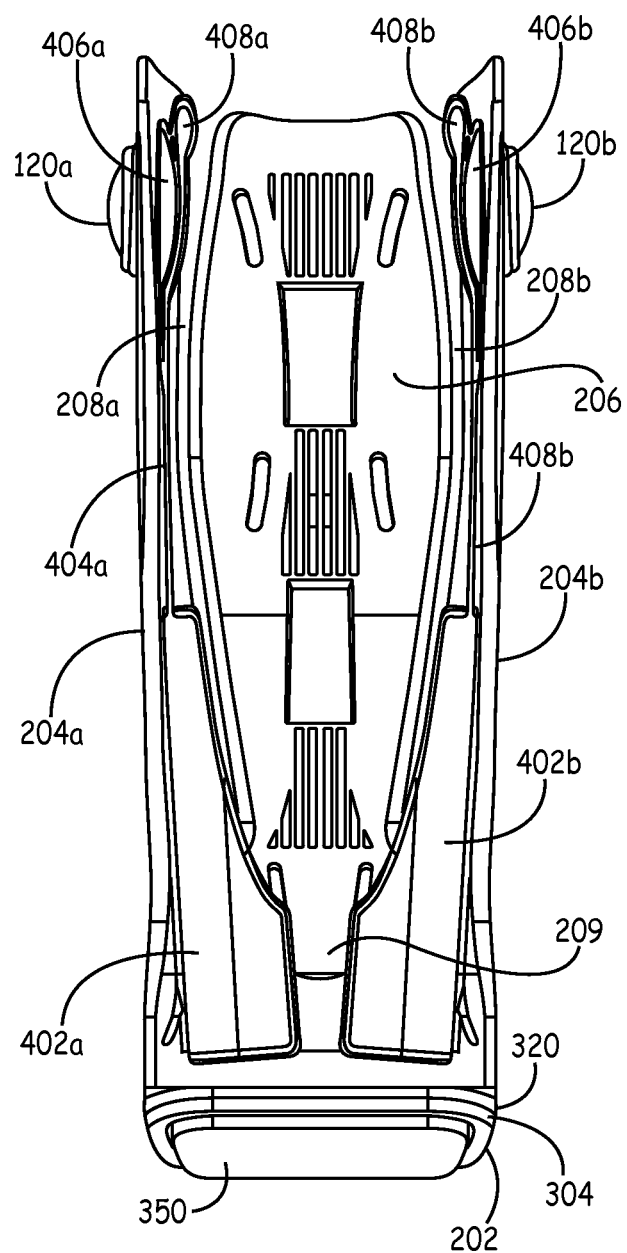
FIG. 10 is a front view of the walker shell of FIG. 2 with the bladder inflation assemblies attached.
Figure 11:
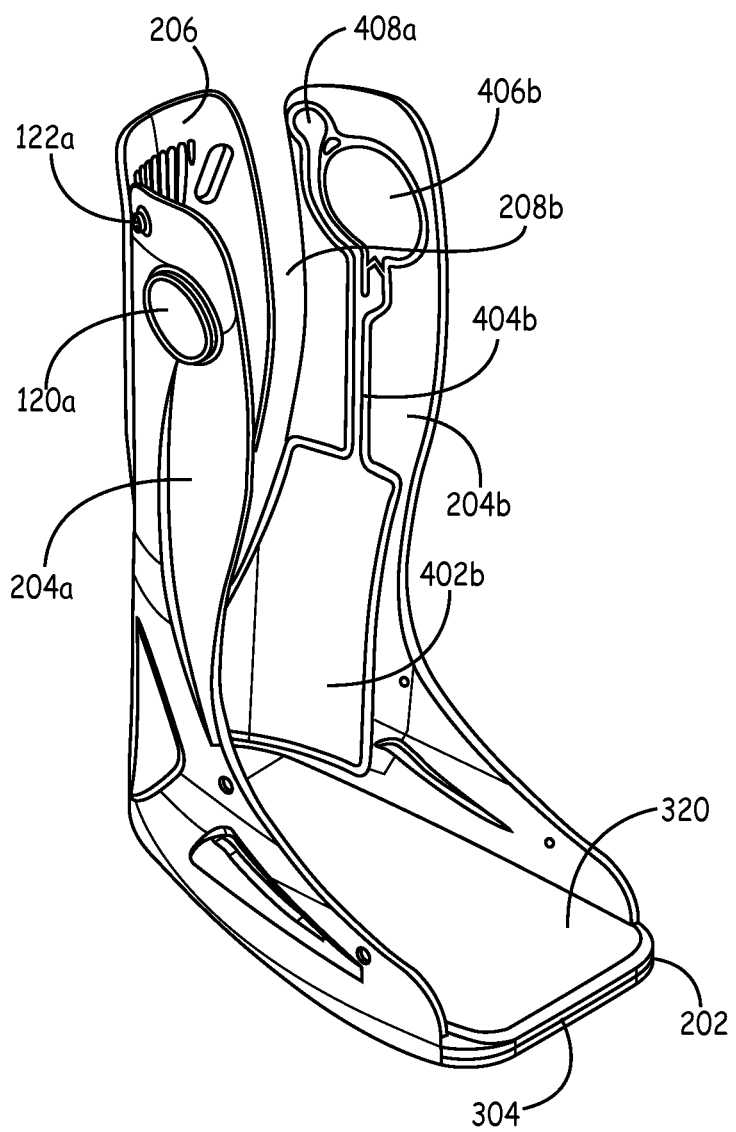
FIG. 11 is a side perspective view of the walker shell of FIG. 2 with the foot support member attached.

The front view of the walker shell 102 in FIG. 10 and the side perspective view of the walker shell 102 of FIG. 11 illustrate the air bladder inflation assemblies 402a and 402b positioned with the walker shell 102. Also illustrated in the Figures are inflation pumps 120a and 120b and air release valve 122b. The inflation pumps 120a and 120b are coupled to the respective pump connection portions 406a and 406b of the bladder inflation assemblies 402a and 402b through the respective air pump passages 220a and 220b in the walker shell 102. The air release valves 122a and 122b are coupled to the respective release valve connection portions 408a and 408b through the respective relief valve passages 222a and 222b. As the positioning of the bladders 402a and 402b illustrated in FIGS. 10 and 11 show, inflating of the bladders 402a and 402b selectively places pressure on a lower leg portion of a patient to provide a selected amount of support.

Figure 12:
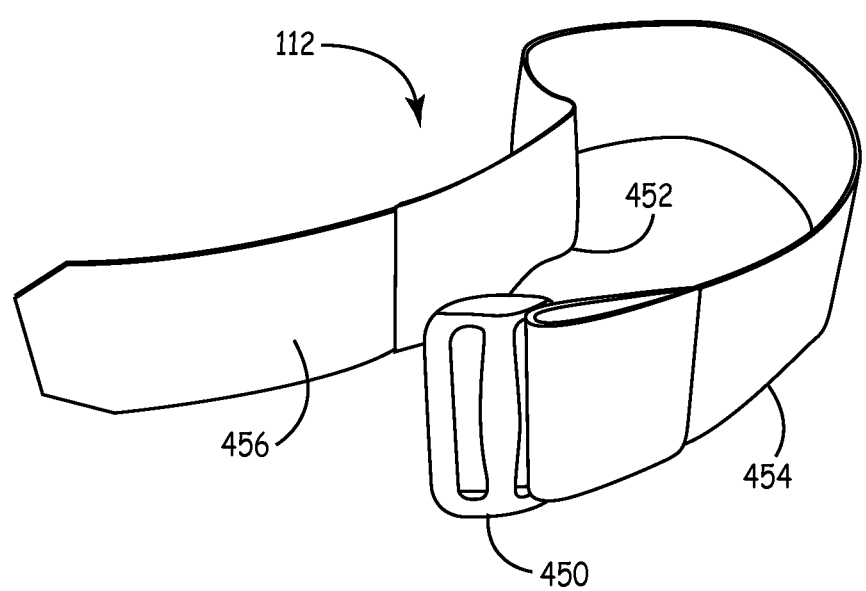
FIG. 12 is a side perspective view of a strap of one embodiment of the present invention.
Figure 13A:
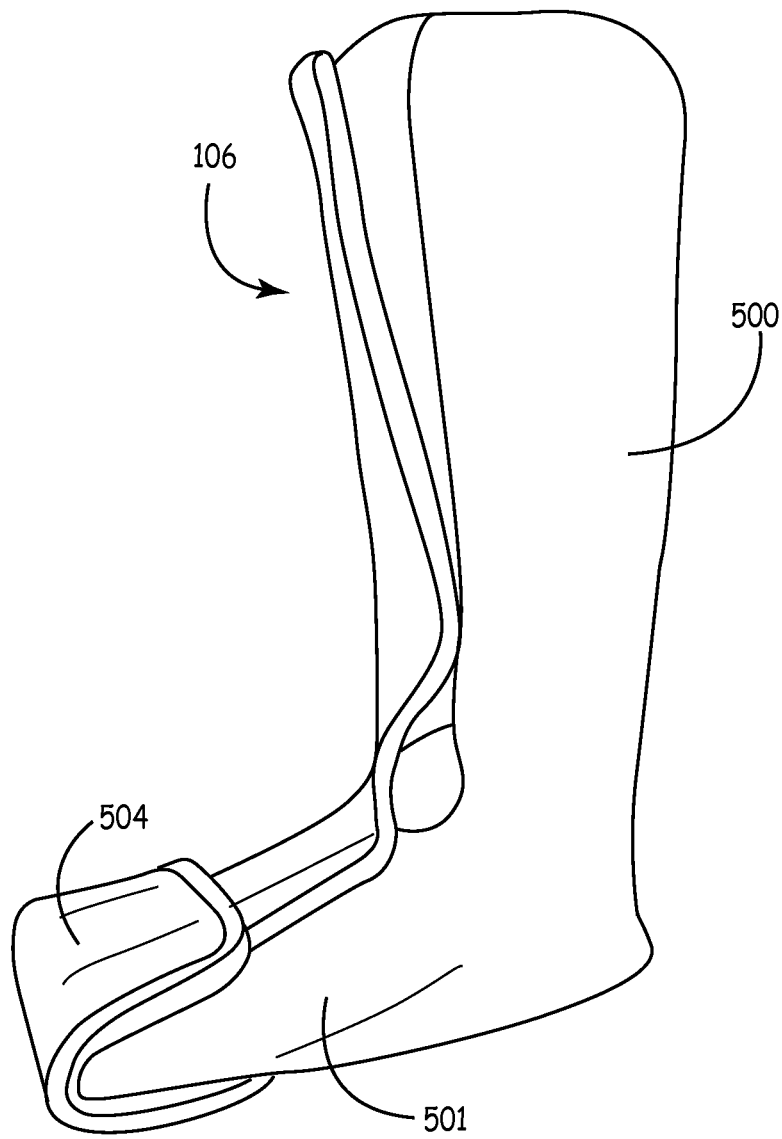
FIG. 13A is an outside side perspective view of an inner lining in a closed configuration of one embodiment of the present invention.
Figure 13B:
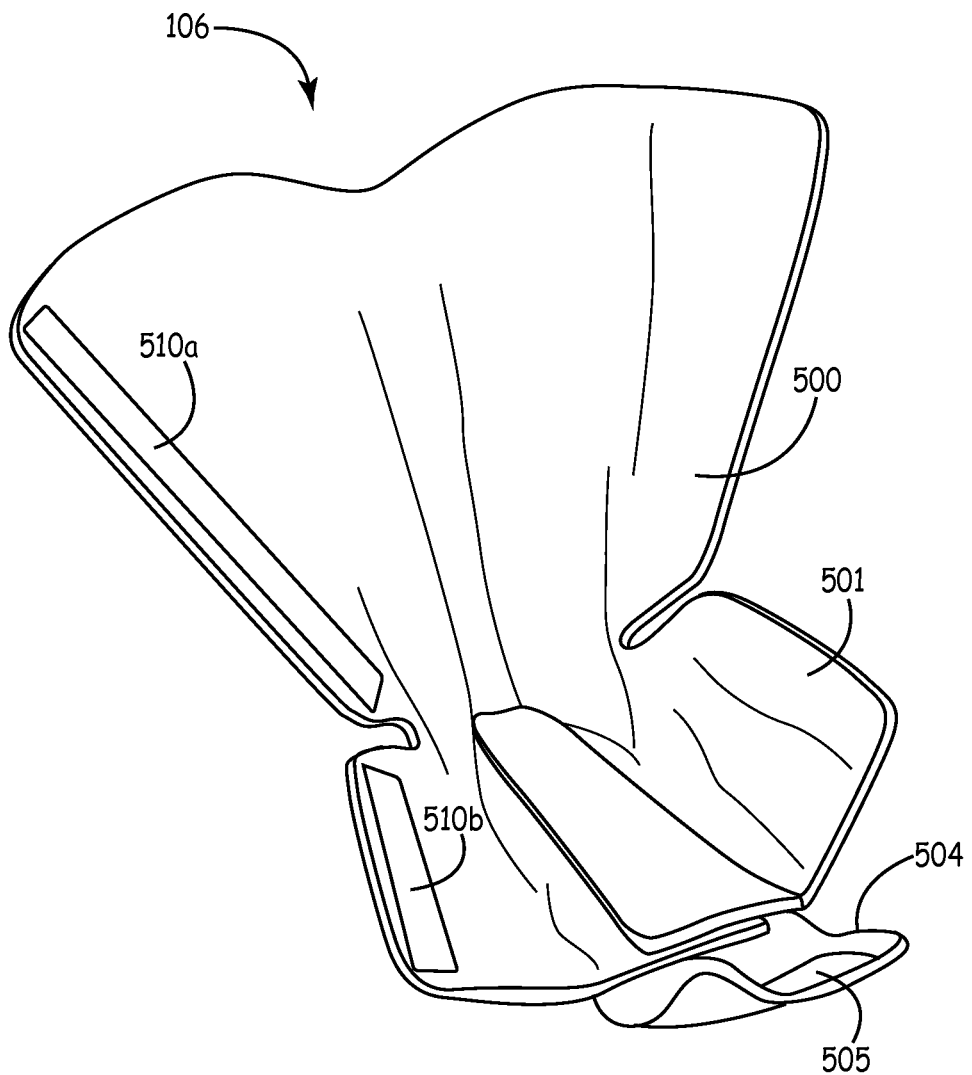
FIG. 13B is an inside side view of the inner lining of FIG. 13A in an open configuration.

FIG. 12 illustrates an example of a strap 112 used to secure the ankle walker 100 on the lower leg of a patient. This strap 112 includes a buckle 450 and a main strap portion 452. The main strap portion 452 in an embodiment is made from a fabric. On one side of the main strap portion 452 is attached a first part 454 of a hook and loop fastener that is configured to be selectively coupled to a second part 456 of a hook and loop fastener that is coupled proximate an end of the main strap portion 452. FIG. 13A illustrates an embodiment of the inner lining 106 that fits into the walker shell 102 to provide cushioning to the patient's lower leg. The inner lining 106 in one embodiment is made from a breathable foam product. The inner lining 106 includes a leg portion 500 and a foot portion 501. The foot portion 501 of the inner lining 106 also includes a toe wrap portion 504. Referring to FIG. 13B, the inner lining 106 illustrated in an open position is shown. In this open position a patient's lower leg is placed into the inner lining 106. The inner lining 106 is then closed around the patient's lower leg. After the patient's lower leg has been positioned within the inner lining 106, the inner lining 106 is secured around the patient's lower leg. In the embodiment of FIG. 13B, securing the inner lining 106 about the patient's lower leg is accomplished with the use of hook connection assemblies 505, 510a and 510b of a hook and loop arrangement that are configured to selectively engage the material of the inner lining 106. In particular, hook connection assembly 510a coupled to a first portion of the leg portion 500 of the inner lining 106 is selectively coupled to a second portion of the leg portion 500 to secure the leg portion 500 of the inner lining around the lower leg of the patient. Hook connection assembly 510b coupled to a first portion of the foot portion 501 of the inner lining 106 is selectively coupled to a second portion of the foot portion 501 to secure the foot portion 501 of the inner lining around the foot of the patient. In addition, hook connection assembly 505 selectively secures the toe wrap 504 to the foot portion 501.

Figure 14:
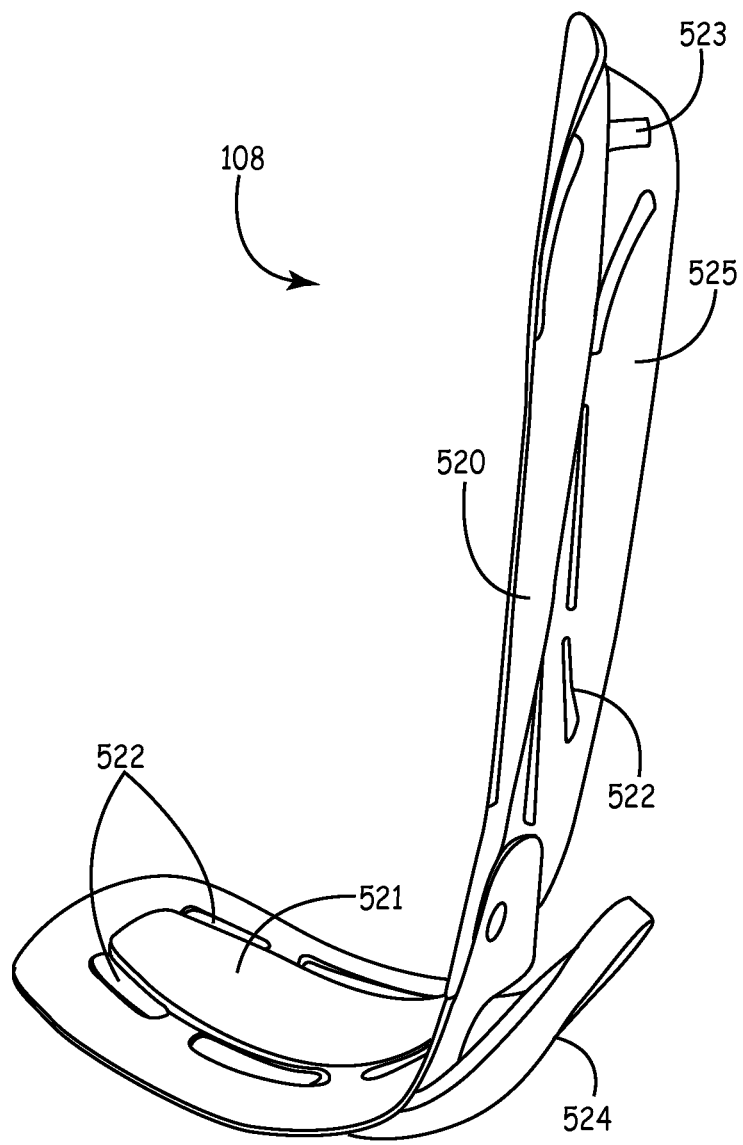
FIG. 14 is a side view of a front panel of one embodiment of the present invention.
Figure 15:
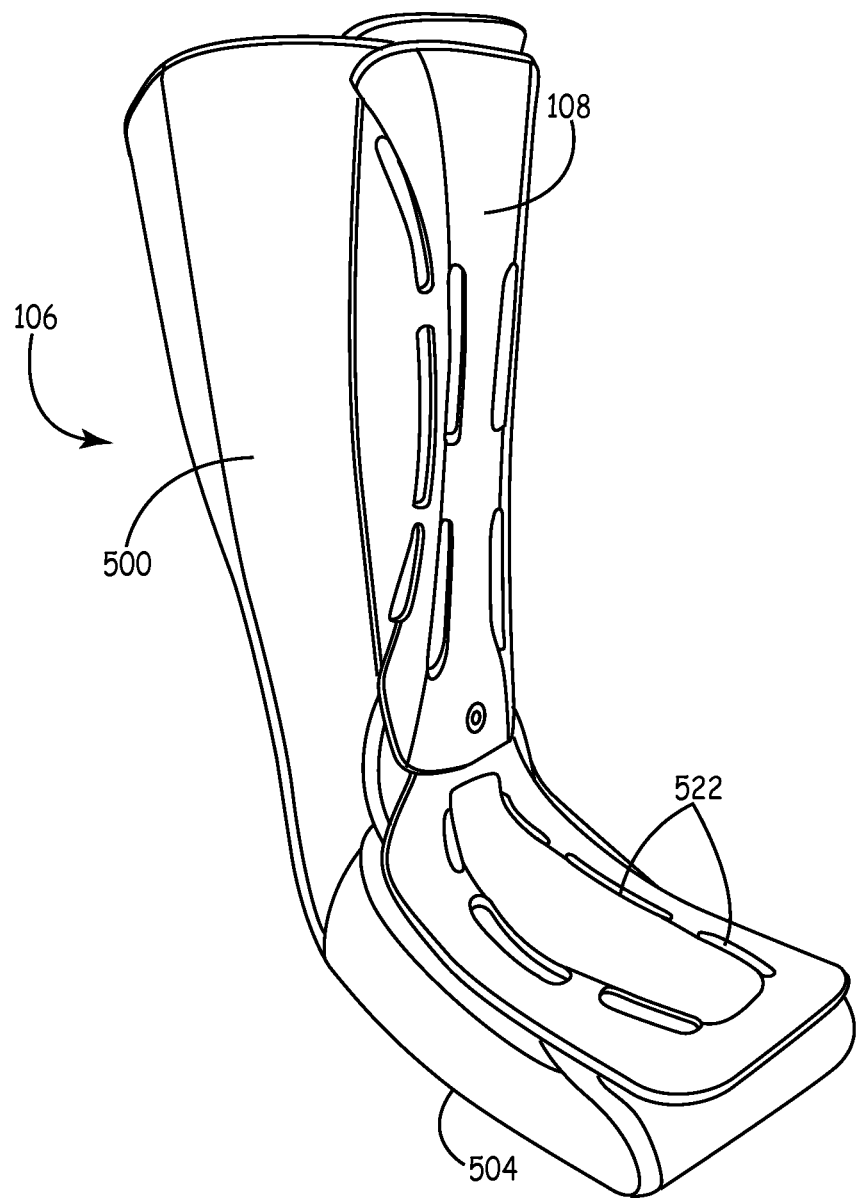
FIG. 15 is a side perspective view of the front panel of FIG. 14 coupled to the inner lining of FIG. 13A.

The front plate 108 is illustrated in FIG. 14. The front plate 108 provides support and protection for the patient's front lower foot. The front plate 108 is made from a relatively stiff material such as, but not limited to, a polymer material. The front plate 108 includes a leg (tibia) plate portion 520 that is coupled to a foot plate portion 521. Throughout the front plate 108 are vents 522 as illustrated in FIG. 14. In the embodiment of FIG. 14, padding 524 is coupled to the back 525 of the front plate 108 to provide extra comfort between the foot and the lower leg. The back 525 of the front plate 108 in an embodiment includes hook connection assemblies 523 of a hook and loop arrangement to selectively couple the front plate 108 to the inner lining 106 as illustrated in FIG. 15. Besides the hook connection assembly 523 on the leg plate portion 520, a similar hook connection assembly 523 is on the back of the foot plate portion 521 to selectively secure the foot plate portion 521 to the foot portion 501 of the inner lining 106. Once the inner lining 106 and the front plate 108 are positioned over a patient's lower leg, the inner lining 106 is positioned in the walker shell 102 and the straps 112a, 112b, 110a and 110b are secured as illustrated in FIG. 1.

Figure 16A:
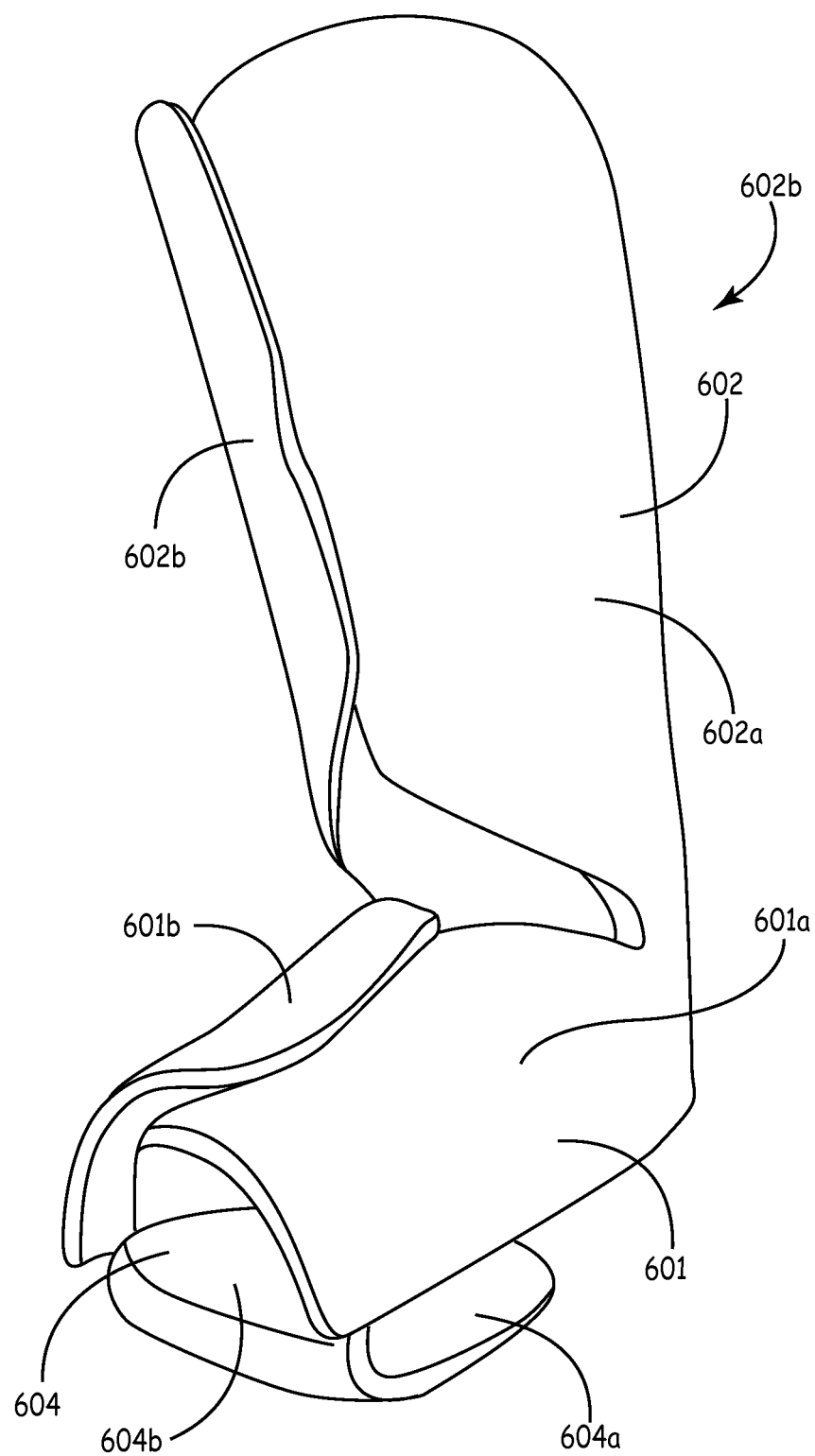
FIG. 16A is an outside side perspective view of another embodiment of an inner lining in a closed configuration of the present invention.
Figure 16B:
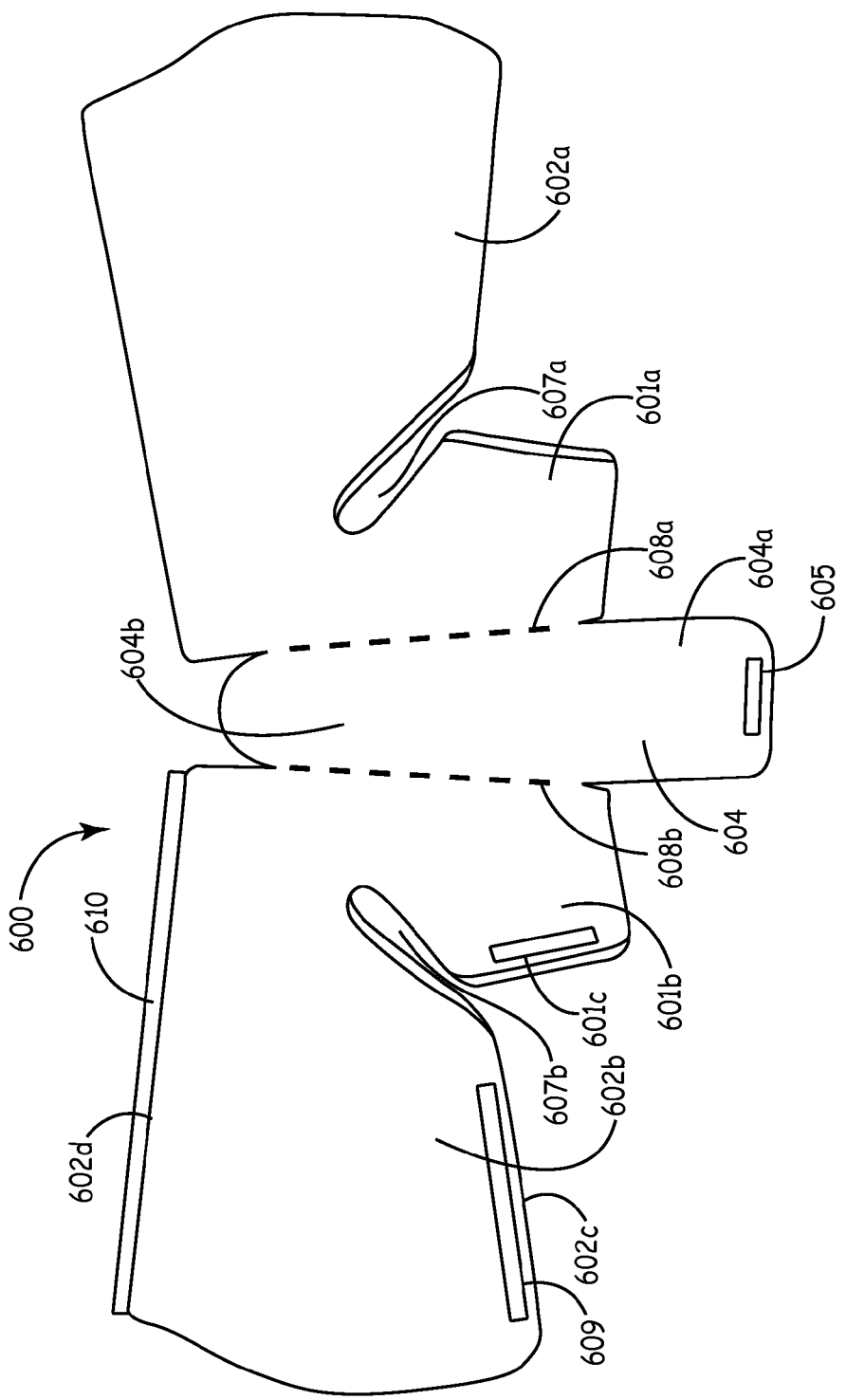
FIG. 16B is an inside top view of the inner lining of FIG. 16A in an open configuration.
Figure 16C:
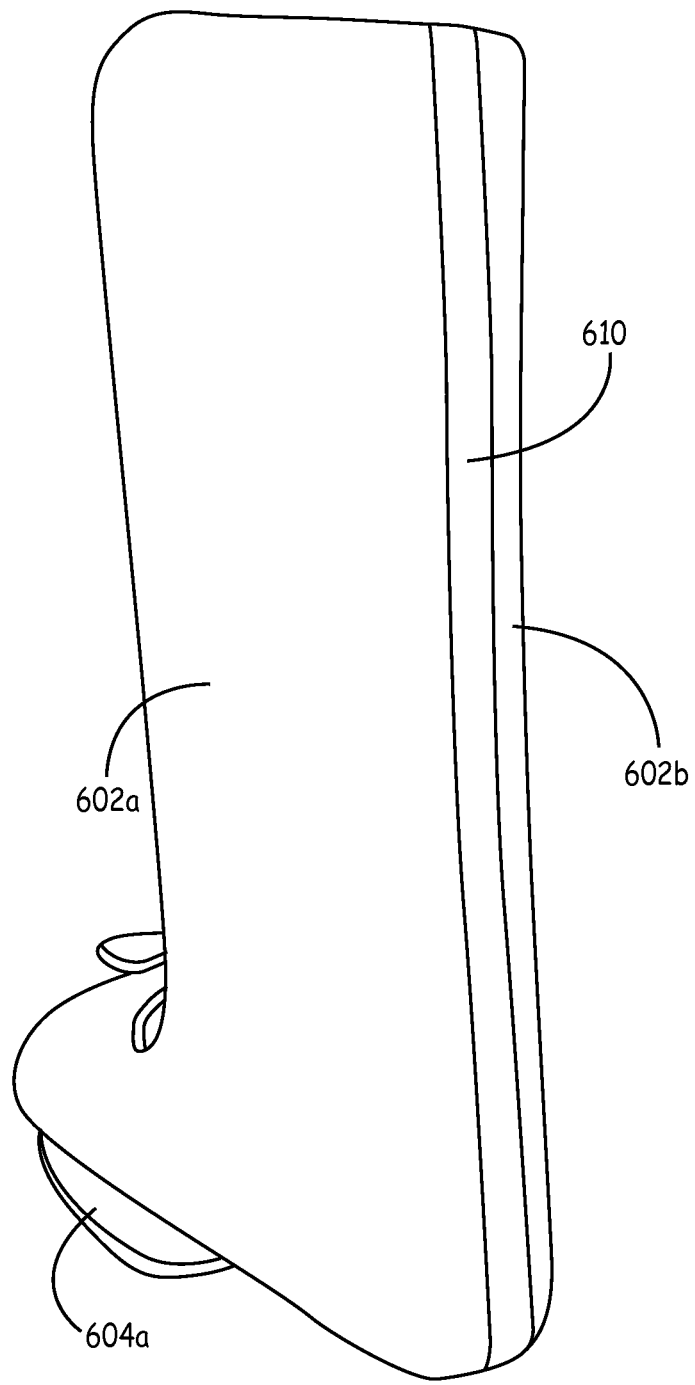
FIG. 16C is an outside rear perspective view of the inner lining of FIG. 16C.

Referring to FIG. 16A a side perspective view of another embodiment of the inner lining 600 is illustrated. The inner lining 600 of this embodiment includes a leg portion 602 and a foot portion 601. This embodiment also includes a toe wrap portion 604a that can either be positioned to cover the toes (as illustrated in FIG. 13B) or wrapped under the foot portion 601 (as illustrated in FIG. 16A) depending on the patient's desire. A top view of the inner lining 600 in an open configuration is illustrated. The advantage of this embodiment is that the inner lining 600 can be formed from a single piece of material. As illustrated in FIG. 16B, the inner lining 600 includes a bottom portion 604 that includes the toe wrap portion 604a and a foot support portion 604b. A toe wrap connection assembly 605 is coupled to the toe wrap portion 604a to selectively couple the toe wrap portion 604a to the foot portion 601 to cover the toes of the patient. The toe wrap portion 604a will have a similar toe wrap connection assembly (not shown in FIG. 16B) on an opposed side to selectively couple the toe wrap portion 604a under the foot support portion 604b when the patient does not want his or her toes covered. The foot portion 601 includes a first foot portion 601a and a second foot portion 601b. A foot connection assembly 601c is used to selectively couple the first foot portion 601a to the second foot portion 601b to wrap the foot portion 610 around the foot of the patient. As illustrated, score lines 608a and 608b separate the foot support portion 604a of the bottom portion 604 from the respective first and second foot portions 601a and 601b of the foot portion 601. The score lines aid in bending the first and second foot portions 601a and 601b in relation to the foot support portion 604a. As also shown in the pattern shown in FIG. 16B, leg portion 602 includes a first leg portion 602a and 602b that extend from the respective first and second foot portions 601a and 601b. Respective slots 607b and 607a are positioned between portions of the first and second leg portions 602a and 602b and the respective first and second foot portions 601a and 601b. A first leg connection assembly 609 is coupled proximate a front edge 602c of the second leg portion 602b and a second leg connection assembly 610 is coupled proximate the back edge 602d of the second leg portion 602b. The first leg connection assembly 609 selectively couples a first front portion of the second leg portion 602b to a front portion of the first leg portion 602a and the second leg connection assembly 610 couples a back portion of the of the second leg portion 602b to a back portion of the first leg portion 602a to fit the leg portion 602 around a patient's leg. In embodiments, the toe wrap connection assembly 605, the foot connection assembly 601c and the first and second leg connection assemblies 609 and 610 are part of a hook and loop connection system designed to selectively hold on to the material of the inner lining 600. Referring to FIG. 16C a back perspective view of the inner lining of this embodiment is illustrated showing how the second leg connection assembly couples the back of the first and second leg portions 602a and 602b together.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

The invention claimed is:

1. A walker shell comprising:
a base configured and arranged to support the weight of a patient using the walker shell,
the base including a top surface and a bottom surface, the bottom surface including a holding rail guide configured and arranged to hold a rail of a sole to maintain the sole in a static position in relation to the base;
a first side panel connected to the base and terminating in a first side panel top edge;
a second side panel connected to the base and terminating in a second side panel top edge, the second side panel positioned across the base from the first side panel; and
a back panel connected to the base and terminating in a back panel top edge, the back panel positioned between the first and second side panels, the first side panel and the back panel having at least one first slot there between, the second side panel and the back panel having at least one second slot there between, the walker shell having a height extending between the base and the first and second side panel top edges.

2. The walker shell of claim 1, further comprising:
the at least one first slot and the at least one second slot extending at least one half the height of the walker shell to allow the back panel to move relative to the first and second side panels to allow for the walker shell to be easily positioned about a patient's calf when the patient is putting on the walker shell.

3. The walker shell of claim 1, further comprising:
a lower foot portion extending upward from the base proximate a portion of an outer perimeter of the base;
the first side panel extending from a first portion of the lower foot portion;
the second side panel extending from a second portion of the lower foot portion; and
the back panel extending from a third portion of the lower foot portion.

4. The walker shell of claim 1, wherein the first and second side panels each have a malleolus concavity positioned to receive a malleolus ankle protrusion of a patient; and
the at least one first slot and the at least one second slot extending to at least one malleolus concavity.

5. The walker shell of claim 1, wherein at least one of the first and second side panels have an air pump aperture and a release valve aperture, at least the air pump aperture located proximate the top edge of a respective first and second side panel.

6. The walker shell of claim 1, further comprising:
the base including at least one foot support passage configured and arranged to hold a foot support in a static position in relation to the base.

7. The walker shell of claim 1, wherein the back panel includes at least one strap guide configured and arranged to receive a strap.

8. An ankle walker comprising:
an ankle shell including,
a base configured and arranged to support the weight of a patient using the ankle walker,
a lower foot portion extending upward from the base proximate a portion of an outer perimeter of the base,
a first side panel extending from a first portion of the lower foot portion,
a second side panel extending from a second portion of the lower foot portion, the second side panel positioned across the base from the first side panel, and
a back panel extending from a third portion of the lower foot portion, the back portion positioned between the first and second side panels, the ankle shell having a first slot separating the first side panel from the back panel and a second slot separating the second side panel from the back panel, the ankle walker having a height extending between the base and an upper edge of at least one of the first and second side panels of the walker shell, at least one of the first and second slots having a height that is at least two thirds the height of the ankle walker, further wherein the base, lower foot portion, first and second side panels and back panel form an ankle shell cavity in which a patient's lower foot is received;
an inner lining configured and arranged to fit within the ankle shell cavity, the inner lining including a bottom portion having a foot support portion and a toe wrap portion, the toe wrap is configured and arranged to have an open position to allow the toes of the patient to be exposed and a closed position that covers the toes of the patient;
at least one bladder configured and arranged to be selectively inflated, the at least one bladder positioned within the ankle shell cavity; and
at least one strap configured and arranged to secure the ankle shell around a patient's lower leg.

9. The ankle walker of claim 8, wherein the at least one of the first slot and the second slot has a height that extends at least to a location where a patient's malleolus would be positioned when using the ankle walker.

10. The ankle walker of claim 8, further comprising:
a front panel configured and arranged to provide support to a patient's front portion of the lower leg, the front panel secured to provide support by the at least one strap.

11. The ankle walker of claim 10, further comprising:
at least one connector configured and arranged to selectively couple the front panel to the inner lining.

12. The ankle walker of claim 8, wherein the inner liner is formed from a single piece of material.

13. An ankle walker comprising:
a base configured and arranged to support the weight of a patient using the ankle walker, the base including a top surface and a bottom surface;
a first side panel connected to the base and terminating in a first side panel top edge;
a second side panel connected to the base and terminating in a second side panel top edge, the second side panel positioned across the base from the first side panel; and
a back panel connected to the base and terminating in a back panel top edge, the back panel positioned between the first and second side panels, the first side panel and the back panel having at least one first slot there between, the second side panel and the back panel having at least one second slot there between, the ankle walker having a height extending between the base and the first and second side panel top edges, further wherein the base, lower foot portion, first and second side panels and back panel form an ankle shell cavity in which a patient's lower foot is received;
an inner lining configured and arranged to fit within the ankle shell cavity, the inner lining including a bottom portion having a foot support portion and a toe wrap portion, the toe wrap is configured and arranged to have an open position to allow the toes of the patient to be exposed and a closed position that covers the toes of the patient, the inner liner is formed from a single piece of material, the inner liner including,
a first foot portion extending from a first portion of the foot support portion of the bottom portion, a first score line separating the first foot portion from the foot support portion,
a second foot portion extending from a second portion of the foot support portion of the bottom portion in an opposed fashion in relation to the first foot portion, a second score line separating the second foot portion from the foot support portion, the first and second foot portions configured and arranged to be selectively coupled around a foot of a patient,
a first leg portion extending from a portion of the first foot portion, and
a second leg portion extending from a portion of the second foot portion, the first and second leg portions configured and arranged to be selectively coupled around a leg of the patient.

* * * * *